(12) United States Patent
Cooper et al.

(10) Patent No.: US 11,751,786 B2
(45) Date of Patent: Sep. 12, 2023

(54) NEUROGENIC BLADDER MONITORING AND ASSOCIATED SYSTEMS AND DEVICES

(71) Applicant: University of Iowa Research Foundation, Iowa City, IA (US)

(72) Inventors: Christopher Cooper, Iowa City, IA (US); Ryan Steinberg, Iowa City, IA (US); Lewis Thomas, Chicago, IL (US); Clifford Curry, Iowa City, IA (US); Eric Pahl, Iowa City, IA (US); Sanam Zarei, Coralville, IA (US); Kayla Jones, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 306 days.

(21) Appl. No.: 16/862,532

(22) Filed: Apr. 29, 2020

(65) Prior Publication Data

US 2020/0390381 A1    Dec. 17, 2020

Related U.S. Application Data

(60) Provisional application No. 62/840,116, filed on Apr. 29, 2019.

(51) Int. Cl.
*A61B 5/20* (2006.01)
*A61B 5/00* (2006.01)

(52) U.S. Cl.
CPC ............. *A61B 5/205* (2013.01); *A61B 5/002* (2013.01); *A61B 5/0004* (2013.01); *A61B 5/6852* (2013.01); *A61B 5/742* (2013.01); *A61B 5/746* (2013.01); *A61B 2560/0431* (2013.01); *A61B 2562/0247* (2013.01)

(58) Field of Classification Search
CPC ....... A61B 5/205; A61B 5/0004; A61B 5/002; A61B 5/6852; A61B 5/742; A61B 5/746; A61B 2560/0431; A61B 2562/0247
See application file for complete search history.

(56) References Cited

U.S. PATENT DOCUMENTS

| | | | |
|---|---|---|---|
| 4,261,360 A * | 4/1981 | Perez | A61M 3/0212 604/118 |
| 8,337,411 B2 * | 12/2012 | Nishtala | A61B 5/205 600/580 |
| 11,653,865 B2 | 5/2023 | Lee et al. | |
| 2006/0074272 A1 * | 4/2006 | DiUbaldi | A61B 18/04 600/29 |
| 2009/0221933 A1 * | 9/2009 | Nishtala | A61B 5/205 600/561 |
| 2018/0110456 A1 * | 4/2018 | Cooper | A61B 5/202 |

FOREIGN PATENT DOCUMENTS

WO    WO 2016154457 A1 *    9/2016

* cited by examiner

*Primary Examiner* — Jonathan T Kuo
(74) *Attorney, Agent, or Firm* — Dentons Davis Brown; Matthew Warner-Blankenship

(57) ABSTRACT

The various embodiments disclosed here relate to systems, methods, and devices for monitoring bladder health via pressure. Certain implementations are directed to patients who require daily catheterization. The various embodiments have at least one tube coupled to a catheter, a pressure sensor and a processor. Further implementations feature an optional pump and measure volume. Certain embodiments include a digital device with a software application capable of displaying the monitored readings.

19 Claims, 26 Drawing Sheets

NEUROGENIC BLADDER MONITORING AND ASSOCIATED SYSTEMS AND DEVICES

CROSS-REFERENCE TO RELATED APPLICATION(S)

This patent application claims priority to U.S. App. No. 62/840,116, filed Apr. 29, 2019, which is hereby incorporated by reference in its entirety under 35 U.S.C. § 119(e).

TECHNICAL FIELD

Neurogenic bladder (NGB) patients require periodic urodynamics (UDS) to monitor bladder function and guide catheterization frequency and medication management. Increased surveillance has improved outcomes in other chronic conditions such as diabetes with home glucose monitoring.

The various embodiments herein relate to systems, methods, and devices for monitoring bladder health of a patient, including real-time monitoring of bladder health of patients who require daily catheterization, including, in some cases, clean, intermittent catheterization up to 15 times each day depending on the patient bladder size, function and/or urine production.

BACKGROUND

Patients with a neurogenic bladder are at increased risk of renal and bladder damage from high-pressure urine storage in their bladder. Myelodysplastic patients with a neurogenic bladder leak point pressure of 40 cm of water or higher on cystometrogram were at highest risk of adverse changes in their ureters and kidneys. These findings guide the current management strategy of adjusting daily intermittent catheterization frequency and anticholinergic dosing to keep bladder storage pressures in a safe range, thereby preventing both irreversible kidney and bladder damage. Urodynamic studies are used to assess bladder storage functions including capacity, compliance, and stability, as well as voiding function in patients with neurogenic bladder. Worsening of these parameters dictates the need for a change in management.

Close monitoring and management adjustments have been associated with improved patient outcomes in a variety of chronic illnesses. For example, diabetic patients routinely monitor their blood glucose levels at home and adjust their diet and insulin dosage based on these home-based measurements. This helps to prevent the development of adverse outcomes such as retinopathy and neuropathy. Frequent measurements also improve patient compliance with health provider's recommendations. In addition, healthcare providers may adjust their recommendations based on home-based data. In a similar fashion, patients with neurogenic bladders may have improved outcomes if they could more frequently monitor and track their bladder pressures.

The current, known procedure utilized by clinicians to monitor the state of patients' bladders and the concomitant changes in bladder pressure with urinary volume readings is called Urodynamic Testing (UDS). This technique involves placing catheters in the bladder and/or rectum, and filling the bladder while measuring the compliance, pressure, and volume in the bladder. Drawbacks of UDS are that it requires an extensive amount of capital equipment, is not readily available in all clinics, is long in duration (a typical test requires 1-2 hours for completion), is expensive (around $4500 for testing and interpretation) and is contingent on factors related to the administration and interpretation of the test by the healthcare team. Another disadvantage is that the test is very invasive for patients, as patients have catheters placed in the bladder and rectum, the bladder is filled with fluid at a set rate while the pressure is continuously monitored, and the patients may be asked to urinate on command in front of the team administering the test. A further disadvantage is that it fails to provide a comprehensive summary of the bladder's condition—UDS only provides a snapshot of a single point in time (i.e. the time of test administration). Since UDS is normally done approximately once a year (though can be performed more or less frequently depending on the severity of the patient's disease), bladder pressure can increase between tests and thus bladder and/or kidney damage can go undetected by both physician and patient for prolonged periods of time. It is not uncommon for physicians to see patients with bladders and kidneys that have 'deteriorated' between their visits. This makes the initiation of any intervention for worsening bladder pressure (whether behavioral, medical, or surgery) a reactive intervention, rather than proactive.

There is a need in the art for improved systems, methods, and devices for monitoring bladder health of a patient. To facilitate this goal, the present disclosure relates to novel devices and related systems and methods relating to bladder pressure monitoring.

BRIEF SUMMARY

Discussed herein are various bladder health monitoring systems and devices. The various systems and devices disclosed herein relate to devices for use in medical procedures and systems. More specifically, various embodiments relate to various medical devices, including handheld pressure monitoring devices including a smaller, handheld pump-free cystomanometer and larger pump-driven cystoelastometer devices and related methods and systems.

In Example 1, a bladder health monitoring device comprising a housing defining an enclosure, a tube disposed through the enclosure, a pressure sensor disposed within the enclosure, and an actuation button configured to initiate the measurement of bladder pressure via the pressure sensor.

In Example 2, the bladder health monitoring device of Example 1, further comprising a coupling component configured to attach to the end of any catheter routinely used for intermittent catheterization.

In Example 3, the bladder health monitoring device of Example 1, further comprising a processor disposed within the enclosure, and a communications component disposed within the enclosure.

In Example 4, the bladder health monitoring device of Example 3, further comprising a PCB disposed within the enclosure and in operable communication with the processor and communications component.

In Example 5, the bladder health monitoring device of Example 3, further comprising memory.

In Example 6, the bladder health monitoring device of Example 1, further comprising a switch, wherein the actuation button is constructed and arranged to actuate the switch and form a pinch valve with the tube in the enclosure upon actuation.

In Example 7, a handheld bladder health monitoring device comprising a housing defining an enclosure, a tube disposed through the enclosure, a pressure sensor disposed within the enclosure, a PCB disposed within the enclosure, the PCB comprising a processor, and a memory component, a communications component disposed within the enclosure, and an actuation button in operable communication with the tube and configured to initiate the measurement of bladder pressure via the pressure sensor as recorded bladder pressure data.

In Example 8, the handheld bladder health monitoring device of Example 7, further comprising a switch in operational communication with the pressure sensor and actuation button and constructed and arranged to initiate pressure measurement upon actuation of the actuation button.

In Example 9, the handheld bladder health monitoring device of Example 7, wherein the pressure sensor is configured to record pressures in the range of about −10 to about 100.0 cmH2O.

In Example 10, the handheld bladder health monitoring device of Example 7, further comprising a signaling mechanism.

In Example 11, the handheld bladder health monitoring device of Example 7, wherein the actuation button is configured to stop the flow of urine through the lumen upon actuation.

In Example 12, the handheld bladder health monitoring device of Example 7, wherein the memory is non-volatile memory.

In Example 13, the handheld bladder health monitoring device of Example 7, wherein the communications component is a Bluetooth® communications component configured to pair to a mobile device for the transmission of recorded bladder pressure data.

In Example 14, a bladder health monitoring system comprising the handheld bladder health monitoring device of Example 7, and a mobile device software application constructed and arranged to display recorded bladder pressure data.

In Example 15, a bladder health monitoring system comprising a tube comprising a lumen, a housing comprising a processor comprising memory, at least one pressure sensor in fluidic communication with the lumen, a pump in fluidic communication with the lumen, and an actuation button, wherein the processor is configured to record bladder pressure data from the at least one pressure sensor when urine has entered the lumen.

In Example 16, the bladder health monitoring system of Example 15, further comprising a fluid detector.

In Example 17, the bladder health monitoring system of Example 15, further comprising a second pressure sensor configured to record vacuum pressure during pumping.

In Example 18, the bladder health monitoring system of Example 15, wherein the device is configured to begin pumping at a first speed, detect the presence of fluid in the tube lumen, stop pumping, measure and record bladder pressure data, and restart pumping at a second speed. In certain implementations of this Example, the second speed is greater than or equal to the first speed.

In Example 19, the bladder health monitoring system of Example 15, wherein the communications component is a Bluetooth® communications component configured to pair to a mobile device for the transmission of recorded bladder pressure data.

In Example 20, the bladder health monitoring system of Example 15, further comprising at least one signaling mechanism.

Other embodiments of these Examples include corresponding computer systems, apparatus, and computer programs recorded on one or more computer storage devices, each configured to perform the actions of the methods. Implementations of the described techniques may include hardware, a method or process, or computer software on a computer-accessible medium.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

BRIEF DESCRIPTION OF THE DRAWINGS

FIG. 9A is a front view of a mobile device operating a software application, according to another exemplary embodiment.

DETAILED DESCRIPTION

Figure 1A:
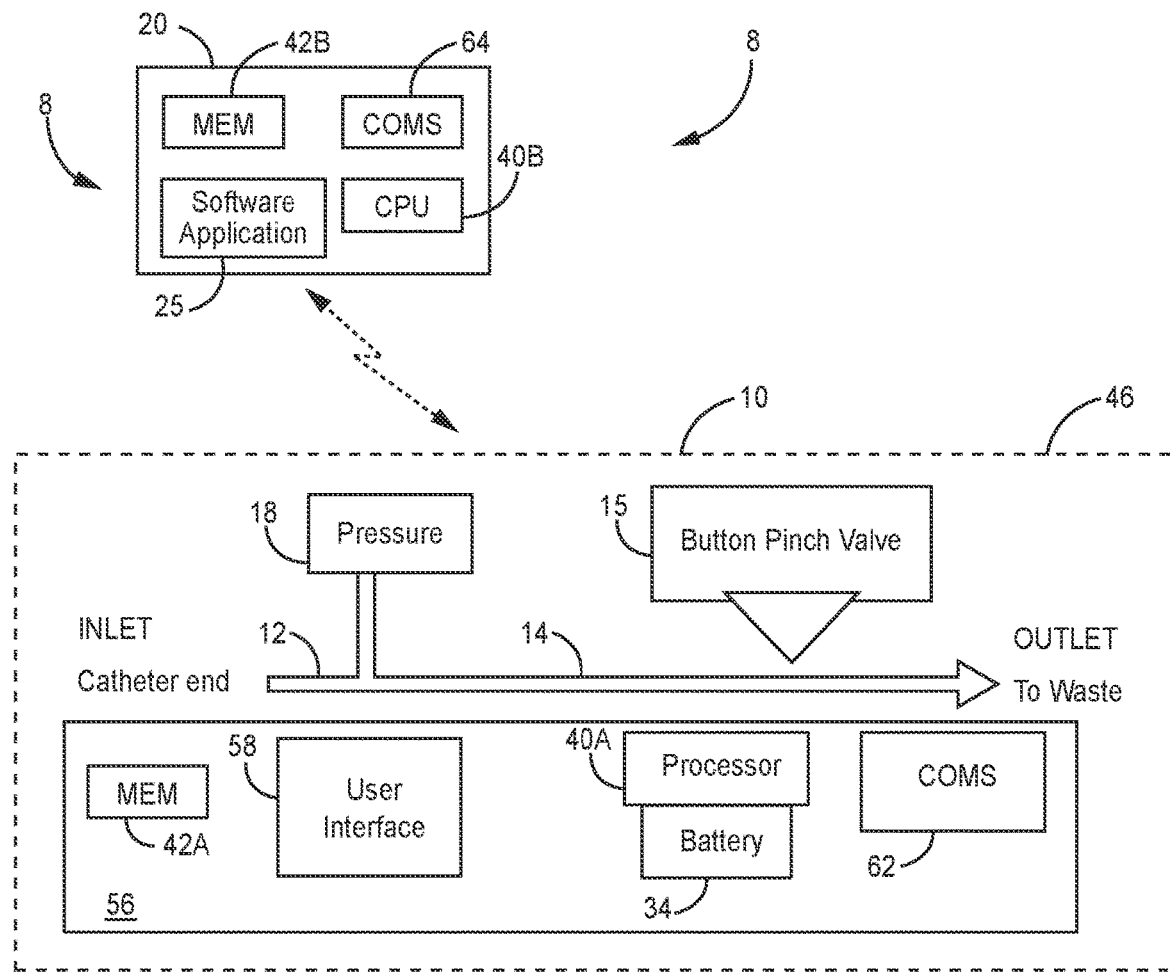
FIG. 1A is a block diagram of a bladder health device without a pump in communication with a digital component, according to an exemplary embodiment.
Figure 1B:
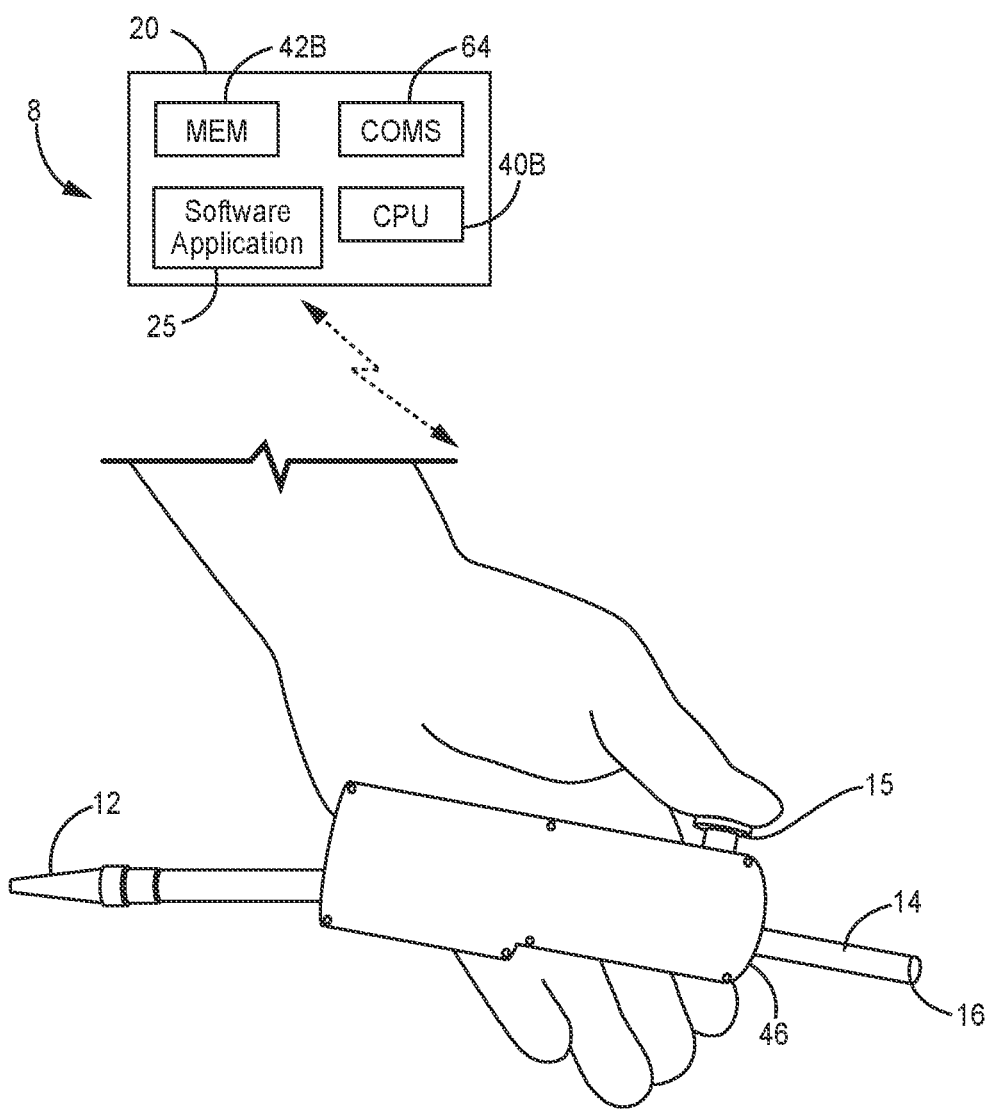
FIG. 1B is a side view of the device and digital component according to the implementation of FIG. 1A.

The various systems and devices disclosed herein relate to pressure-monitoring devices for use in medical procedures and systems. More specifically, various embodiments relate to various bladder health monitoring devices, including devices that function as handheld pressure monitoring devices such as cystomanometers and/or cystoelastometers and related methods and systems.

It is understood that the various embodiments of these bladder monitoring devices and related methods and systems disclosed herein can be incorporated into or used with any other known medical devices, systems, and methods.

For example, the various embodiments disclosed herein may be incorporated into or used with any of the medical devices and systems disclosed in U.S. patent application Ser. No. 15/560,830 filed on Sep. 22, 2017, which claims priority to International PCT Application No. PCT/US16/24057 filed on Mar. 24, 2016, which claims priority to U.S. Provisional Application No. 62/137,633 filed Mar. 24, 2015 and entitled "Bladder Health Monitoring Systems and Related Methods and Devices," all of which are hereby incorporated herein by reference in their entireties for all purposes.

Various embodiments of the pressure monitoring device 10 is shown generally throughout FIGS. 1A-8 and 10A-11G. In various implementations, the pressure monitoring device 10 is a handheld device which attaches to the end of any catheter, measures the bladder pressure, and records the value with time and date. As shown in FIGS. 1A-4, certain implementations of the pressure monitoring device 10 lack an optional pump 30 and therefore operate as cystomanometers 10 measuring pressure. As shown in the implementations of FIGS. 5A-7, in various implementations the pressure monitoring device 10 has an optional pump 30 and operates as a cystoelastometer 10, measuring pressure and/or volume. It will be readily appreciated by those of skill in the art that the various implementations of the pressure monitoring device 10 are directed to the monitoring of bladder pressure and health.

As such, various embodiments relate to a system 8 have a pressure monitoring device 10 and a digital component 20 such as a mobile device 20. In the various implementations, the pressure monitoring device 10 is a bladder monitoring device 10 that can couple to a patient's urinary catheter and thereby measures the pressure in the bladder at the time of urinary catheter insertion as well as optionally the volume obtained from catheterization and the time and date of each catheterization for implementations like those of FIGS. 5A-8. The digital component 20 is a separate system or processor running a software application 25 such as a mobile device application, electronic medical health records system, or other electronic database or records system that is configured to interface with the digital component 20. This software application 25 (also referred to herein as an "algorithm" or "module") that has flexible function settings for extracting information for compiling, packaging, processing, evaluating the various bladder health readings of the system 8 for analysis and display. Certain of the embodiments are also equipped to measure volume, as is shown in the implementations of FIGS. 5A-8.

The pressure monitoring device 10 according to these implementations further has one or more command logic board such as a printed circuit board ("PCB") (shown for example in FIGS. 3, 6 and 10A-11G at 56) having a variety of integrated circuits mounted on either side and/or computing components such as processor, or CPU 40A and/or memory 42A and other components understood to be necessary to effectuate the measurements, recordings and other hardware aspects of the described processes.

The mobile device 20 according to these implementations also has a computing components such as processor, or CPU 40B and/or memory 42B and other components understood to be necessary to effectuate the measurements, recordings and other hardware aspects of the described processes and execution of software.

These processors 40A, 40B are configured to store the recorded bladder pressure data from the pressure sensor component 18, along with date and time data relating to the recorded bladder pressure data (collectively the "recorded bladder pressure data"). In certain embodiments, the processors 40A, 40B are also configured to transmit the compliance, pressure, optionally volume and other data wirelessly, or by direct connection, to the digital component 20 as discussed in further detail below. The processors 40A, 40B are also configured to communicate wirelessly, according to certain embodiments, thereby allowing for transmission of the bladder health data from the device 10 processor 40A to the mobile device 20 processor 40B.

As such, as shown variously in the drawings, the pressure monitoring device 10 can record and store the digital information (pressure, optionally volume, time and date readings and the like) and wirelessly transmit the information to the digital component 20 through paired communications components 62, 64. In one embodiment, the mobile device application is an iPhone®, iPad® or Android® app and the wireless transmission occurs via Bluetooth®, Bluetooth® Low Energy (or Bluetooth® 4.0), cellular communications such as LTE 4G or 5G, WiFi or other known communications technologies.

In one embodiment, the processors 40A, 40B are CPU that is a computer processing unit 40A, 40B or a central processing unit 40A, 40B. Alternatively, the processor 40A, 40B can be an Arduino board, a microprocessor, a computer, or any other known type of processor or processing unit that can be configured to assist with the operation of a medical device such as the device disclosed or contemplated herein. In further embodiments, a plurality of CPUs can be provided and operationally integrated with one another and the various components. FIGS. 10A-11G depict exemplary configurations of PCBs according to the various embodiments, wherein FIGS. 10A-10D are an exemplary implementation of a PCB for the embodiments of FIGS. 1A-4B and FIGS. 11A-11G are an exemplary implementation of a PCB for the embodiments of FIGS. 5A-7.

Further, it is understood that one or more of the processors 40A, 40B can be configured via programming or software to control and coordinate the operation of the sensor component(s) 18 (in the implementations of FIGS. 1A-8) and the optional pump 30 (in the implementations of FIGS. 5A-8) to optimize operation of the system 8.

In certain embodiments the software application 25 is configured to output the time and date of each catheterization as well as bladder pressure (FIGS. 1A-4B) and bladder pressure and volume (FIGS. 5A-8) readings and/or bladder compliance (FIGS. 1-8). In addition, the application can also have an alarm function, providing feedback to the patient, caregiver, physician, or other person when a threshold is exceeded. For example, in one embodiment, if bladder pressure or optional volume and/or compliance readings worsen such that any or all of those parameters increase to the point of reaching a critical pressure or volume threshold indicative of bladder damage, then the mobile device application will trigger an alarm or notification of some kind, thereby causing the patient to consult his or her physician or take other appropriate steps. In addition, the alarm or notification of some kind can trigger the generation of an automatic electronic message to the treating physician, as well as upload a similar electronic message to the patient's file in a hospital's electronic medical record system. Alternatively, the application can be configured to trigger an alarm when one or more catheterizations are not performed in a timely fashion. This application can also permit the physician, caregiver, or patient to make adjustments to various settings, such as pump speed, catheterization thresholds and schedules, as well as pressure, volume, or compliance thresholds with the mobile device application.

Turning to the drawings and embodiments in greater detail, various implementations of the device 10 shown in FIGS. 1A-4, have a catheter coupling component 12 and tubing 14 to facilitate urine flow and record pressure via a transducer 18 without the use of a pump. As shown in the implementations of FIGS. 1A-1B and elsewhere, the device 10 further comprises a pressure sensor 18 or pressure transducer 18 or pressure monitoring component 18 and an actuation button 15. Various implementations can include a known pressure sensor 18, such as an NXP Differential/Gauge pressure sensor or other similar devices known to the skilled artisan. In these implementations, no pump is provided.

In the implementation of FIG. 1A the processor 40A is operably coupled to the pressure sensor component 18, communications components 62 and other electronic components, such as an optional signaling mechanism 58.

To power the electronic components, various implementations the device 10 have a battery 34 that can be a lithium-ion battery, though other types of battery are of course possible.

That is, various of these implementations further comprise a signaling mechanism 58, which can be an LED light, an audio speaker such as a buzzer, a LCD screen or other known device used to communicate to the user that a reading has been taken. These other electronic components 56 can be operationally integrated with the pressure sensor component 18 and/or processor(s) 40A, 40B as would be apparent to one of skill in the art.

In certain implementations, the pressure sensor component 18 is positioned in and through the wall of the tube 14 such that a portion of the sensor component 18 is positioned within the lumen 16 of the tube 14. As such, the sensor component 18 can come into contact with fluid in the lumen 16 and thus is in fluid communication with the urinary catheter tubing via the catheter coupling component 12. According to one embodiment, the pressure sensor component 18 is configured to detect pressure—for example static or dynamic fluid pressure—and transmit the recorded bladder pressure data to the processor(s) 40A, 40B (discussed further below). In exemplary embodiments, the sensor component 18 is sensitive and reliable within the range of about −10 to about 100.0 cmH$_2$O, using a differential pressure measurement between current atmosphere and pressure detected within the lumen 16.

It is understood that in these implementations, the pressure transducer 18 is used to measure the inlet pressure, which should be closely related to the bladder pressure. The device 10 according to these implementations thereby provides accuracy for this pressure range in a compact, easy-to-use design.

Figure 2A:
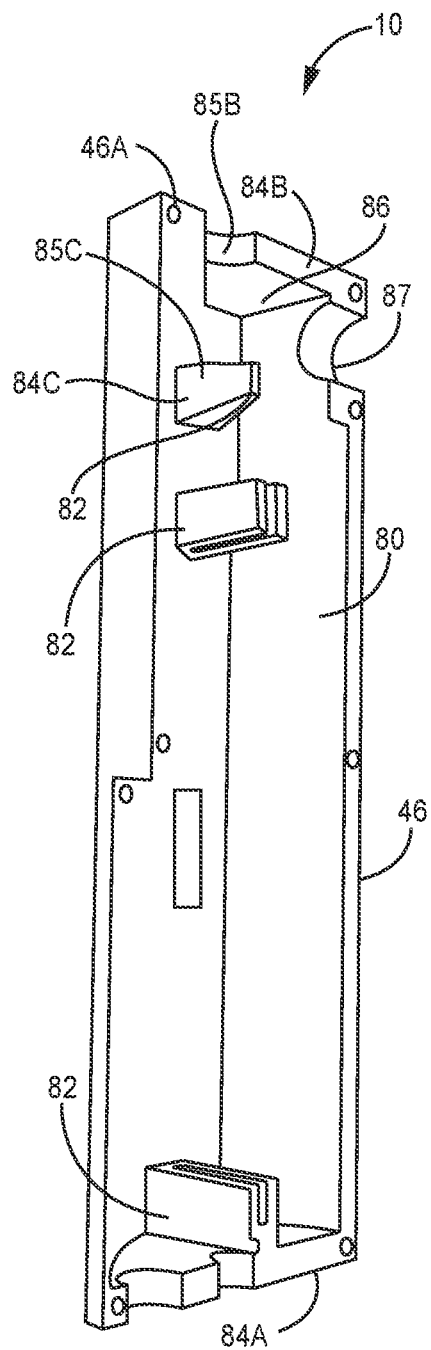
FIG. 2A is a perspective view of another housing portion of a pressure sensing device, according to one embodiment.
Figure 2B:
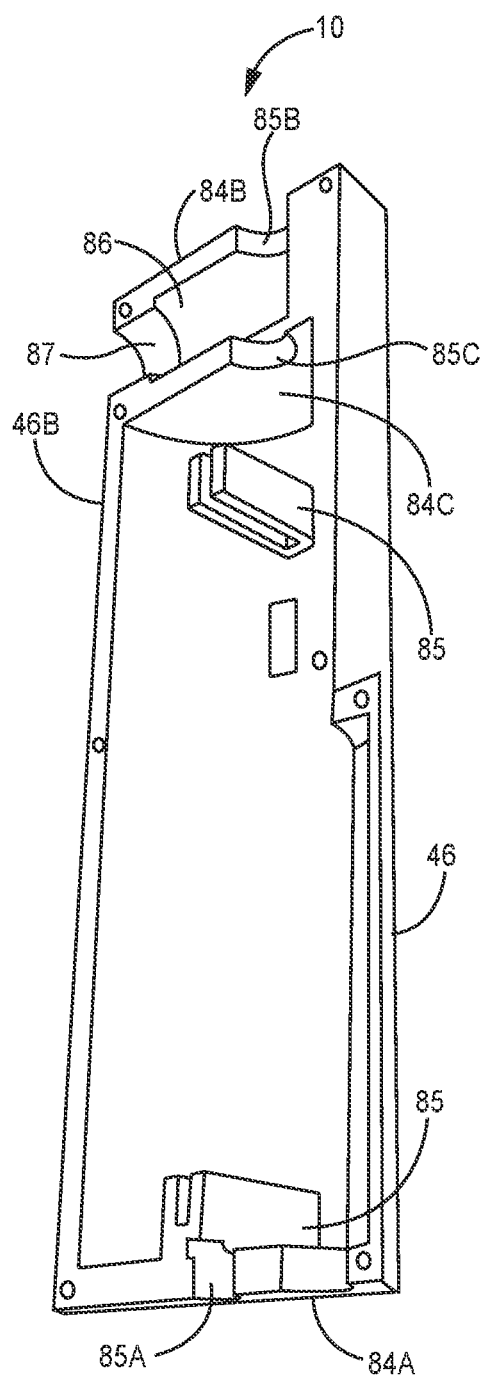
FIG. 2B is a perspective view of another housing portion of a pressure sensing device, according to one embodiment.

As shown in the embodiments of FIGS. 2A-2B, the pressure sensor component 18, processor 40A and/or other hardware and computing components can be disposed within a container or housing 46. The housing 46 can help prevent damage to these components 18, 40A during use and further can help to maintain structural integrity of the overall device 10. In various implementations, the housing 46 can be opened to replace the batteries 34 held within the bladder health monitoring system 8.

The housing 46 according to various implementations comprises several housing portions 46A, 46B that define an enclosure 80 when the housing portions 46A, 46B are affixed to one another, such as via fasteners (not shown). The enclosure 80 comprises several structural aspects to secure and support the various internal components of the device 10. For example, in the implementations of FIGS. 2A-2B, a plurality of PCB supports 82 are provided to support and secure the printed circuit board(s) ("PCB") (shown in FIG. 5 at 56) having, for example, the processor 40, communications component 62, memory 42 and other electronics in place.

As is also shown in the implementation of FIGS. 2A-2B, first 84A and second 84B end enclosing portions are provided, as well as one or more central enclosing portions 84C are provided, each having tube openings 85A, 85B, 85C defined therein for passage of the tube (shown elsewhere at 14) therethrough.

In the implementation of FIGS. 2A-2B, the second end 84B and central 84C enclosing portions further define a button enclosure 86 which also comprises a button opening 87 defined in the housing 46. The button enclosure 86 houses and supports the button 15 for function, as described herein.

Continuing with FIGS. 2A-2B, in various implementations, the material of the tube 14 is transparent, semi-transparent or translucent such that in use, the user is able to visually establish that urine has entered the tube 14 within the enclosure 80 and then be cued to actuate the button 15. It is appreciated that the user can be alerted to the presence of urine in the device through a variety of other transparent or translucent components, as would be readily apparent to those of skill in the art.

Therefore, in use according to these implementations, the catheter coupling component 12 is attached to the end of the urinary catheter (not shown). It is appreciated that in these implementations, urine can flow freely through the device until the button 15 is pressed by the user. Once urine is visualized in the device outflow tubing, the user presses the button, which pinches the tubing and ceases urinary flow.

Figure 2C:
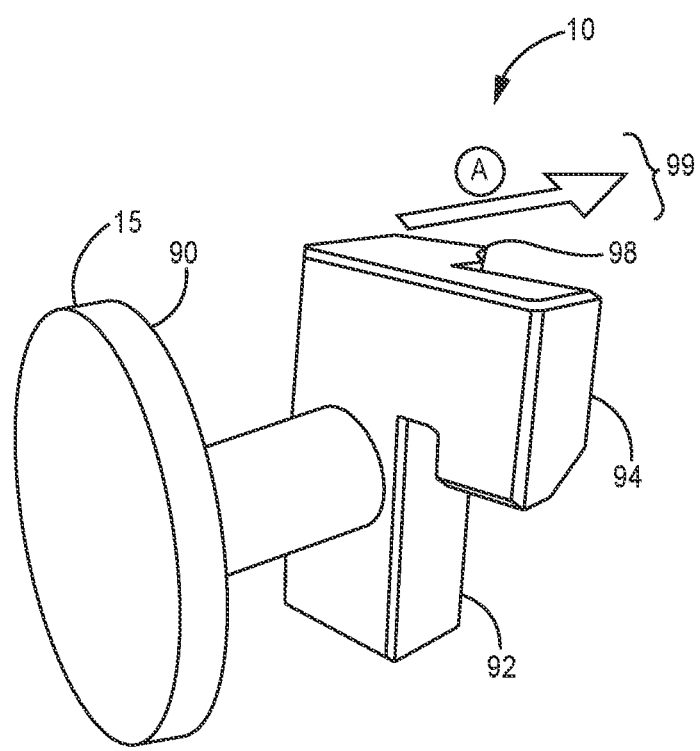
FIG. 2C is a perspective view of an actuation button, according to one embodiment.
Figure 3:
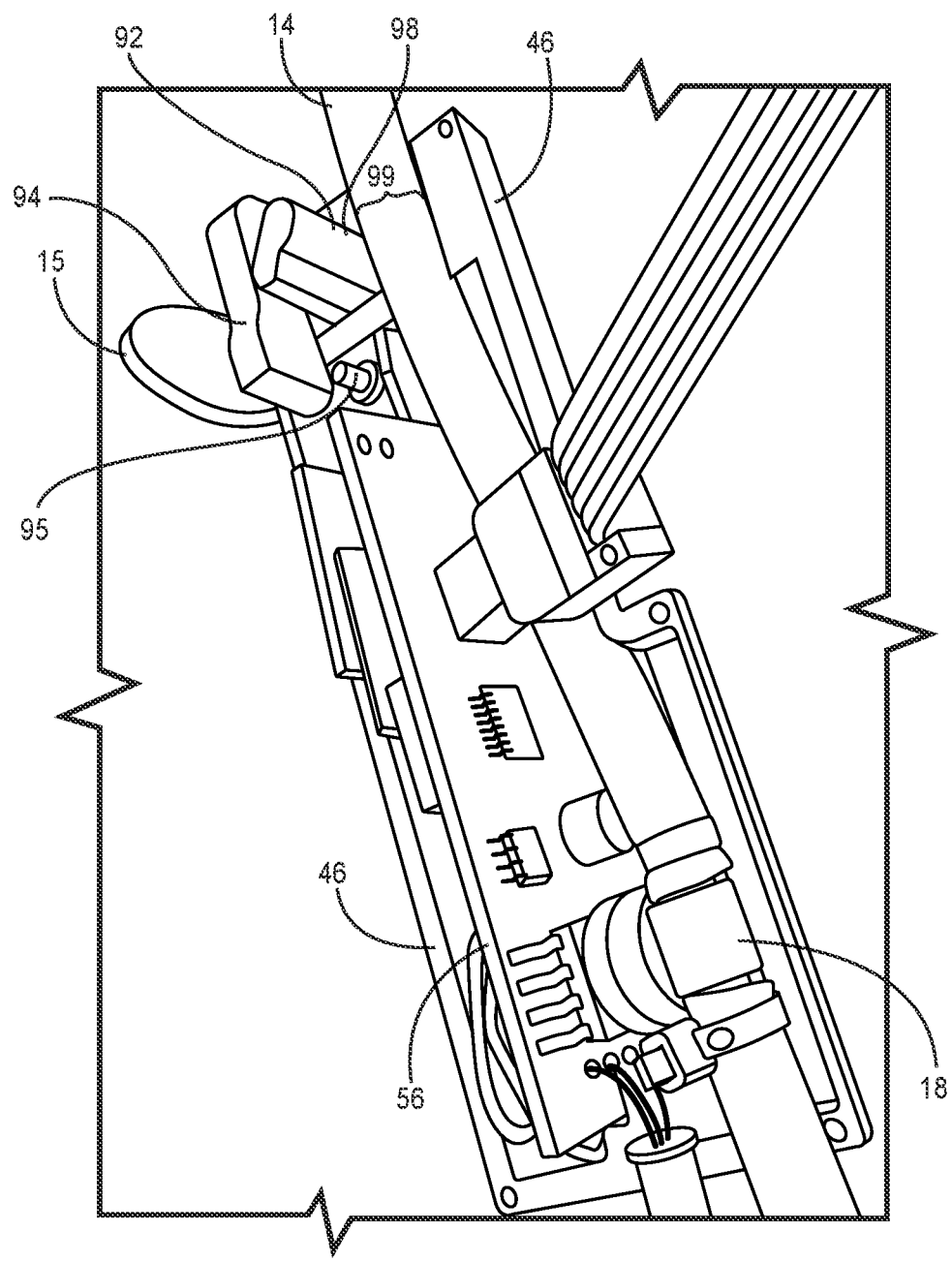
FIG. 3 is a perspective view of the internal components of a pressure sensing device, according to one embodiment.

An implementation of the actuation button 15 is shown in FIG. 2C. In this implementation, the button 15 has a plunger 90 that is configured to be operated by the user pressing, for example, their thumb or other finger on the plunger 90 to depress it into the button enclosure 86 through the button opening 87. A closing member 92 is provided opposite the plunger 90 that has an optional protrusion 98 and is configured to rest against the tube and, when actuated, seal the tube through the force applied by the user to the plunger 90 as a pinch valve 99, also shown via reference arrow A.

In the implementation of FIG. 2C, a switch actuation portion 94 is further provided that is constructed and arranged to actuate a switch 95 disposed within the enclosure 80 (shown in FIG. 3), thereby triggering the pressure measurement by the pressure transducer 18. It is appreciated that in these implementations, the actuation of the pinch valve 99 and the switch 95 occur substantially contemporaneously, though it is also readily appreciated that in various alternative implementations the length and positioning or orientation of the various components can be varied to alter the timing or sequencing of the valve 99 and switch 95 actuations.

The switch 95 according to these implementations is in operable communication with the pressure transducer 18 and is configured to initiate pressure measurement by the transducer 18. It is appreciated that if the device 10 is held at about the same level as the bladder, the pressure at the end of the closed catheter will be approximately the same as the pressure inside the user's bladder.

In various implementations the pressure measurement takes approximately one second, and the signaling mechanism 58 can be configured to provide user feedback on the progress of the measurement. It is readily appreciated that alternate durations ranging from fractions of a second up to several seconds or 10 or more seconds may be required, and that the alert provided by the signaling mechanism 58.

After the pressure is measured, the user releases the button 15, which allows urine to resume flow through the device 10 and for the bladder to be drained. In various implementations, the device 10 saves the recorded bladder pressure data with a timestamp in a storage medium such as non-volatile memory 42A. It is appreciated that the memory 42A is capable of storing hundreds or thousands of measurements. It is further appreciated that timestamping the recorded bladder pressure data in the device for storage and/or transmission can be performed via numerous methods appreciated in the art, such as an integrated circuit or the CPU 40A/PCB 56.

Figure 4A:
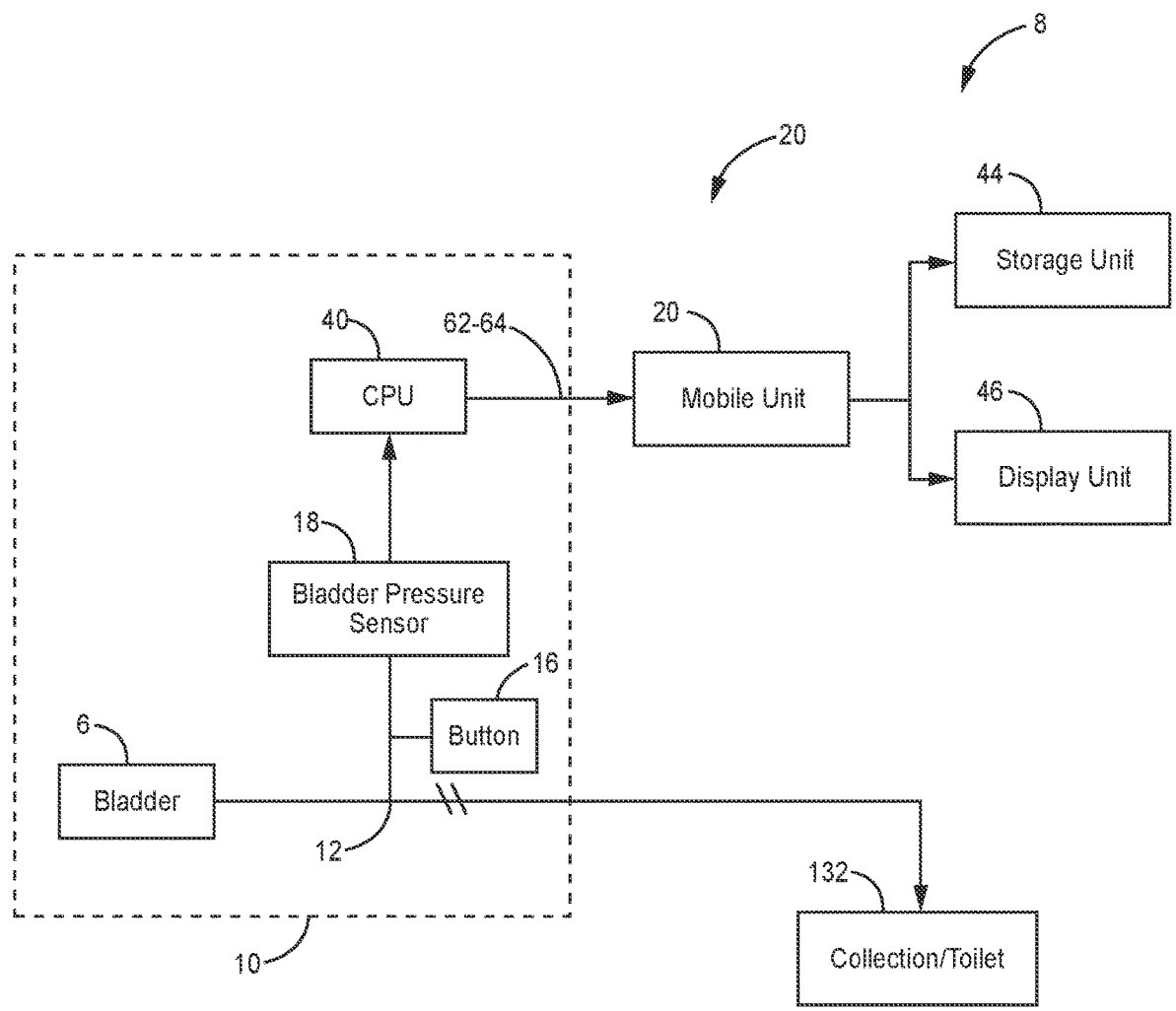
FIG. 4A is a block diagram of a bladder health device without a pump in communication with a digital component, according to another exemplary embodiment.

As shown in FIG. 4A, in use according to certain implementations, the patient's bladder 6 is in fluidic communication with the sensor 18 by way of the connector and tube 14 before the urine is expelled for collection in, for example a toilet 132. In these implementations, the sensor 18 is in electronic communication with the processor 40A, which in turn is in communication with a mobile device 20. The mobile device 20 can have a storage unit 42B and a display unit (shown in FIGS. 9A-9B). As discussed above, the recorded bladder pressure data transmission (line 35) can occur wirelessly through paired communications components 62, 64. Further, in exemplary embodiments, the time and date of each time the device system 8 is connected to a catheter and is in use is recorded by way of the processor 40A and optional memory 42A.

Figure 4B:
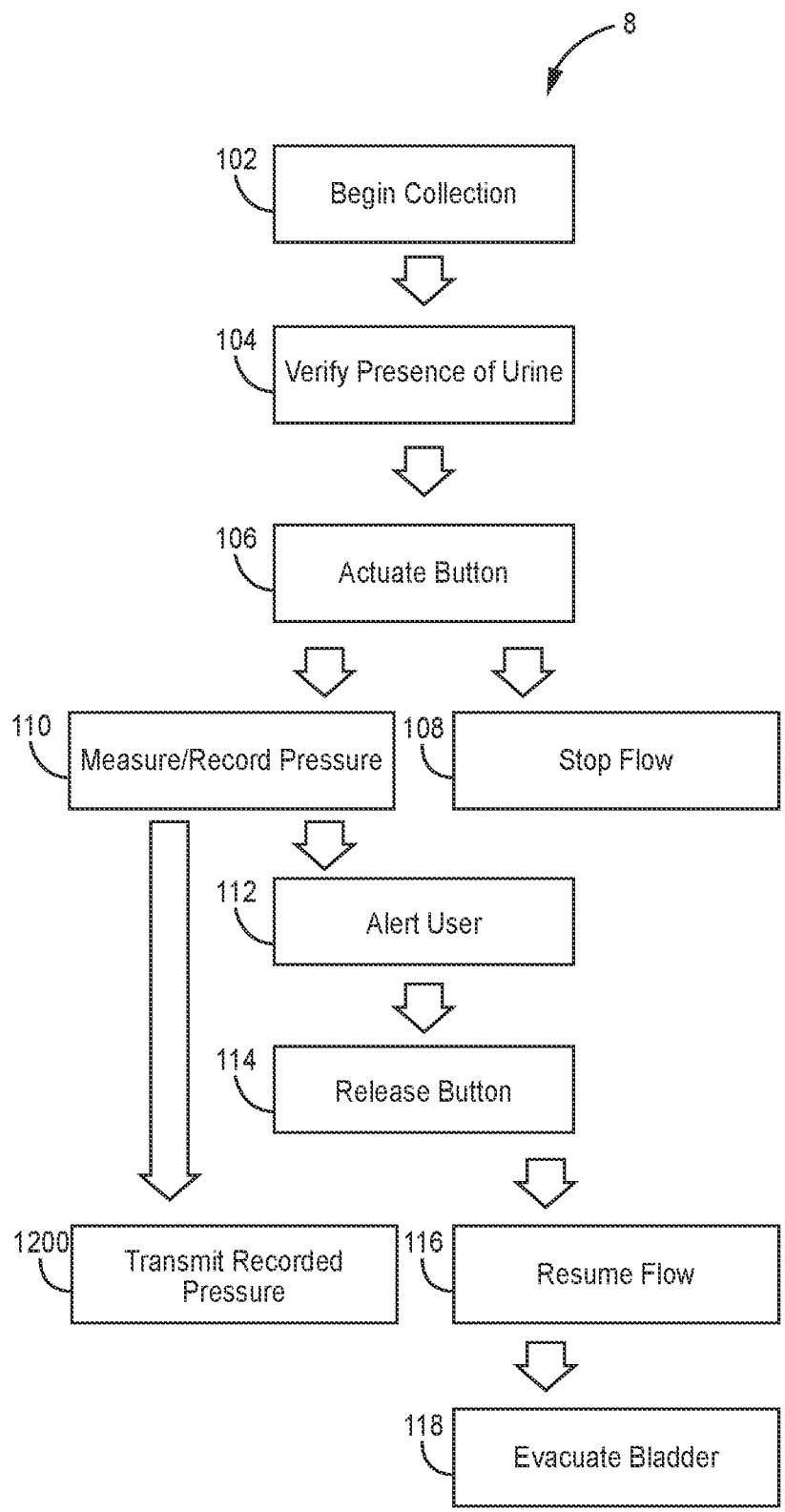
FIG. 4B is a flow chart showing of the bladder health device of FIG. 4A in use.
Figure 5A:
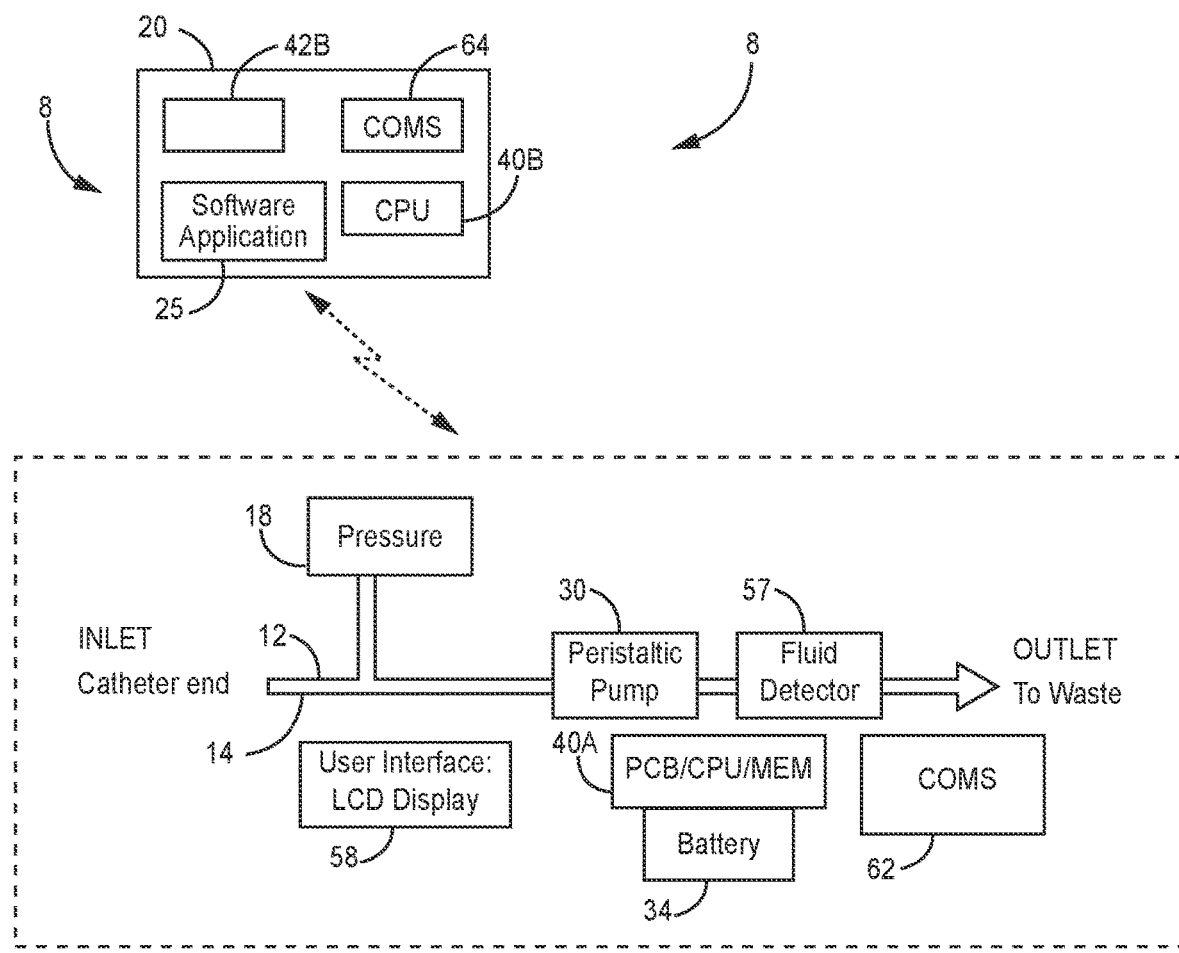
FIG. 5A is a block diagram of a bladder health device with a pump in communication with a digital component, according to an exemplary embodiment.
Figure 5B:
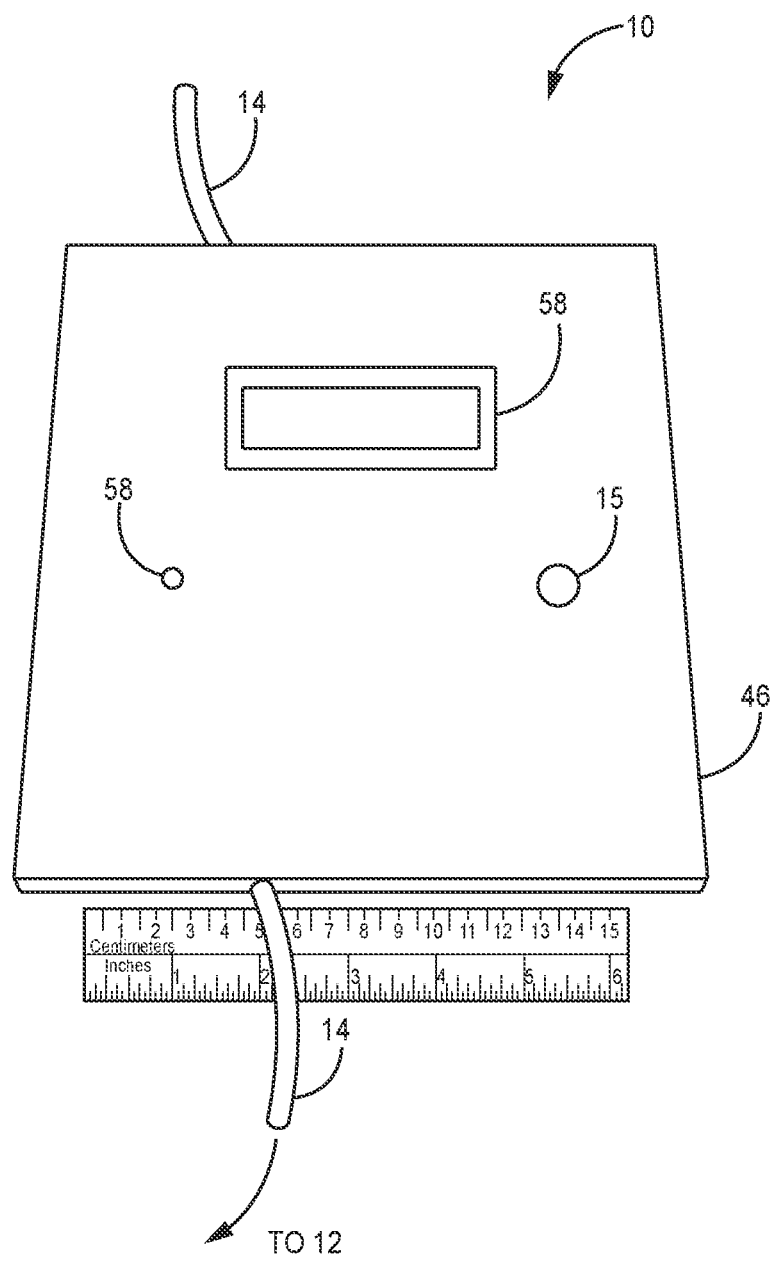
FIG. 5B is a top view of the device and digital component according to the implementation of FIG. 5A.

In use, and as shown in the implementations of FIGS. 4A-4B, once the user is catheterized, collection begins (box 102) and the user then verifies the presence (box 104) of urine in the device 10, such as by viewing it through the tube 14 as was described in relation to FIGS. 2A-2B.

When urine has entered the device 10, the user is able to actuate (box 106) the button 15, thereby stopping flow (box 108) and initiating the pressure measurement (box 110), such as via the switch 95 (shown in FIG. 3) to generate recorded bladder pressure data. It is appreciated that such recorded bladder pressure data can include date, time, measured pressure the like.

Following the pressure recording, the system 8 alerts the user (box 112), such as via the signaling mechanism 58 shown in FIG. 1A, to release the button (box 114) and resume flow (box 116) through the device for evacuation (box 118).

As shown in FIGS. 5A-8, various implementations of the device 10 having an optional pump 30 can operate as an cystoelastometer 10 configured to measure the above parameters such as pressure, as well as urine volume, while actively evacuating urine via the optional pump 30. In these implementations, recorded bladder pressure data is stored and transmitted wirelessly to a digital device 20 such as a smart phone 20 or tablet 20 as described in relation to FIGS. 1A-4. There, a novel software application stores, displays, and transmits data to a secure hospital server, as described below. It is appreciated that these devices 10 allow the patient to be able to monitor their own bladder pressures on a more frequent and routine basis, facilitating improved management of their neurogenic bladder with subsequent improvement in their health.

Figure 6:
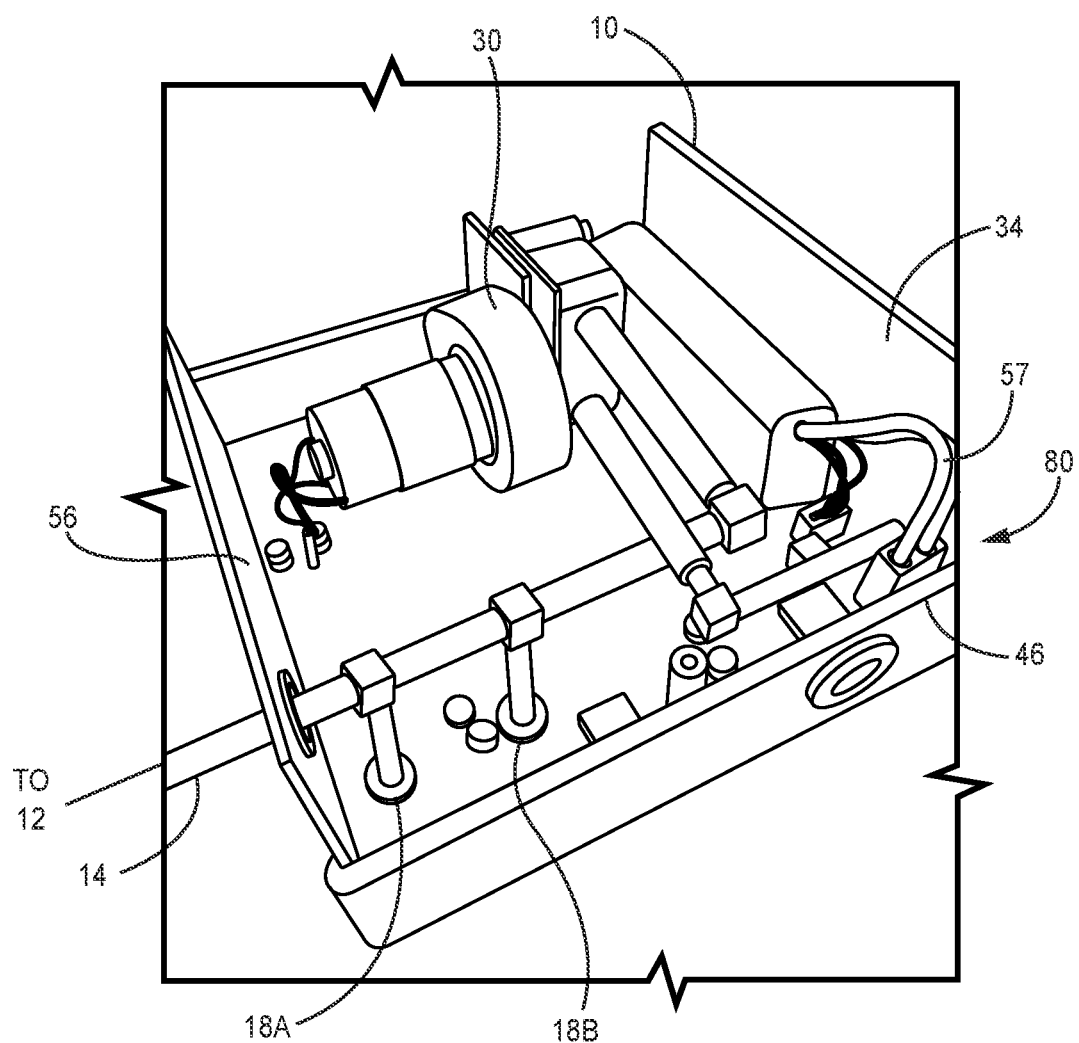
FIG. 6 is a perspective view of the internal components of a pressure sensing device having a pump, according to one embodiment.

As shown in FIG. 6, the device 10 housing 46 according to these implementations features an enclosure 80 housing internal components such as the PCBs 56 having computing components such as processor, or CPU 40A and/or memory 42A and other components understood to be necessary to effectuate the measurements, recordings and other hardware aspects of the described processes.

As shown in the implementation of FIG. 6, the tube 14 is in fluidic communication with at least one pressure transducer 18A, 18B and in this implementation a pressure transducer 18A constructed and arranged to record pressure and is configured to respond to pressures in the about 0 cm to about 100 cm H2O range. In these implementations, a pressure transducer 18B is also used to monitor the suction at the inlet when the pump is running and is configured to respond to vacuums in the range of about milliliters per minute. Various implementations can include known pressure/vacuum sensors 18A, 18B such as the aforementioned NXP Differential/Gauge pressure sensor or other similar devices known to the skilled artisan. Further sensors and ranges are of course possible and would be readily appreciated by those of skill in the art.

The tube is also in fluidic communication with a fluid detector 57, such as an optical fluid detector 57. Other fluid detector types would be readily apparent to those of skill in the art.

Each of these components and the optional pump 30 and battery 34, as well as the button 15, and display 58 are in operational communication with a PCB 56 comprising memory 44A, processing 42A and communications 62 components constructed and arranged for carrying out the functions of the device 10 for static fluid pressure measurements, as have been described above and in relation to FIG. 7.

Instead of the pinch valve of the embodiments of FIGS. 1A-4B and elsewhere, various implementations of the pressure device 10 having a pump 30 utilize a pump 30 such as a peristaltic pump 30 to control the flow of urine through the device 10. The speed of the pump 30 is controlled and/or based on the pressure at the inlet 12 to the device 10.

In use, the system 8 according to these implementations comprises a series of optional steps that can be performed in any order. One exemplary implementation is shown in FIG. 7, though each of the optional steps may be omitted, and the steps may be performed in any order, as would be appreciated by those of skill in the art.

In certain implementations, after the system 8 is initiated via the actuation button (box 200) (shown in FIG. 5A at 15), the pump is started (box 202) and the catheter is connected (box 204).

Figure 7:
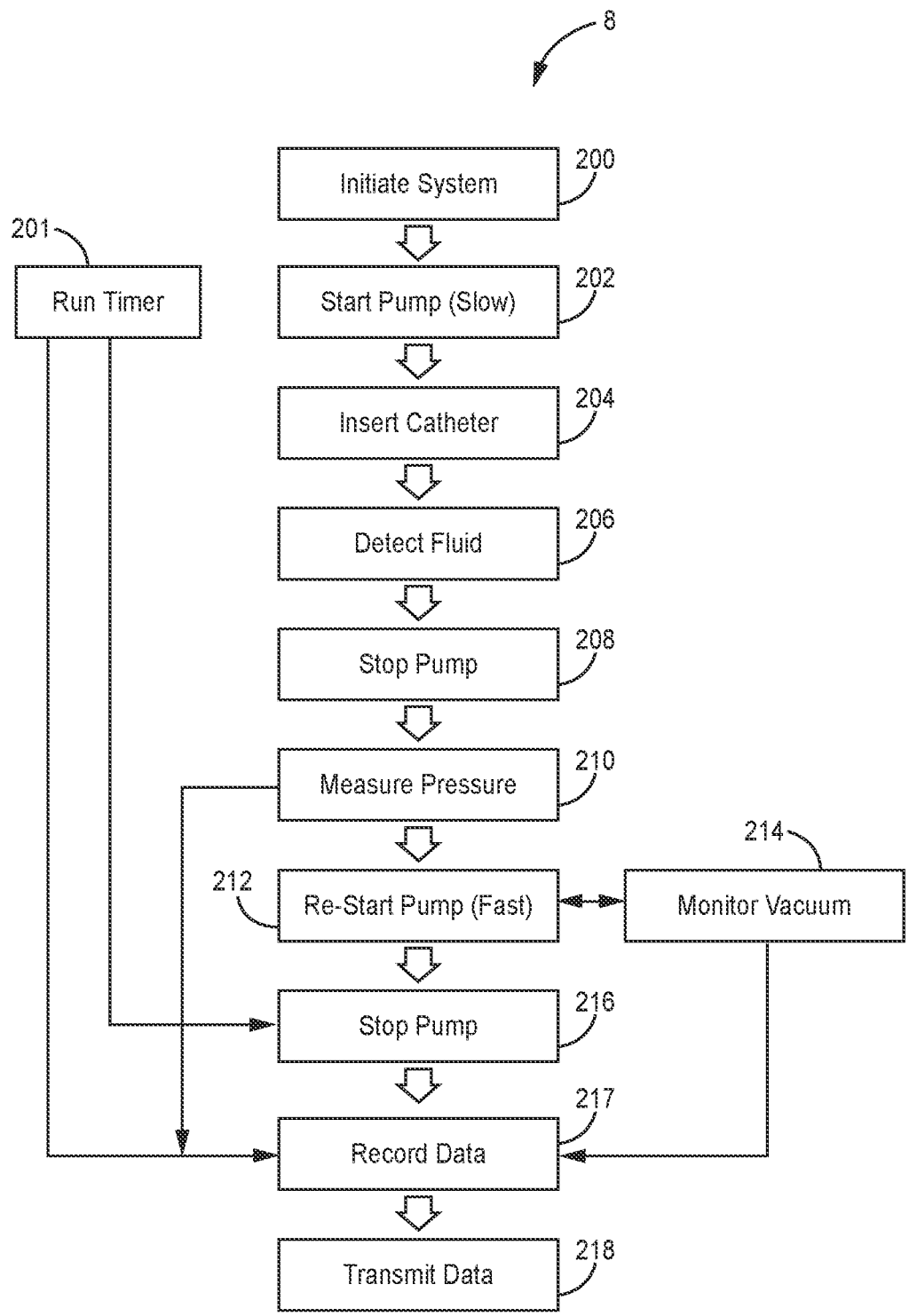
FIG. 7 is a flow chart showing of the bladder health device of FIG. 6 in use.

In implementations like that of FIG. 7, this initial pumping step (box 202) is performed at a low speed so as to pull a relatively low vacuum, such as between about 5 and about 395 milliliters per minute. That is, the pump (shown in FIG. 6 at 30) runs at first speed which is a relatively slow rate to pull the urine out of the bladder and into the catheter and tube 14. Further implementations utilize alternate pump speeds ranging from less than 1 to about 400 milliliters per minute or less than 1 to about 200 milliliters per minute or less than 1 to about 600 milliliters per minute or more, but it is appreciated that slower pump speeds can be advantageous in loading the lumen with urine prior to the fluid detector so as to allow for the stop of the pump with minimal amounts of urine extending through the lumen past the fluid detector.

In various implementations, a timer (box 201) is also started. It will be appreciated that in these implementations, it is desirable to have a total time run for the evacuation of the bladder at which point the entire process will be terminated. For example, the user may wish to set the total run time to about 5 minutes or some other time ranging from a few seconds to 10 or more minutes that will ensure that the pump is stopped and that no errors, misconnections or leaks have occurred and/or that the device is not damaging the user. As such, the timer according to these implementations is in operable communication with the pump and constructed and arranged so as to provide a failsafe stop on the pump after a specified time threshold has been reached. Continuing with the implementation of FIG. 7, in an optional step, the fluid detector (shown at 57 in FIG. 6) detects fluid and the pump is stopped (box 208). The pressure is measured (box 210) and recorded bladder pressure data is recorded, which can include pressure, date, time and, in implementations featuring a pump can include volume, pump speed, pump cycle counts and other recorded volumetric data.

Optionally, the pump is restarted (box 212) such that urine continues to flow through the device 10. In various implementations, the second pump speed in the restarted or second pumping (box 212) is higher than the first pumping (box 202) to speedily evacuate the bladder. Certain implementations can operate at about 400 milliliters per minute, though other speeds would of course be appreciated by those of skill in the art as described elsewhere herein. It is appreciated again that a wide range of second speeds are possible, but that it can be advantageous to pump at a higher speed after the pressure has been measure to speed evacuation of the patient's bladder within a given period of time, for example about 30 seconds or about 2 minutes or about five minutes so as to ensure timely evacuation prior to the expiration of the timer, (box 201). In simpler embodiments, one pumping speed such as about 200 or about 400 mL/min can be used for all pumping steps. It is further appreciated that in any event, the processor can be configured to count pumping cycles and/or times so as to allow for the estimation of volume on the basis of the presences of fluid and the size of the lumen.

In various implementations, the system 8 further optionally monitors the vacuum level and stops the pump if the vacuum level exceeds or falls below certain established thresholds, such as about minus 300 cmH2O. the device 10 monitors the pressure at the pump 30 inlet in real-time. It will be appreciated that as the bladder collapses, the suction of the pump 30 causes the vacuum at the pump inlet to rise which is detected by the transducer.

In various embodiments, the pump 30 is used to accelerate the evacuation time of catheterization, maintain a constant negative pressure, and contribute to an almost constant flow rate of the fluid moving through the lumen.

After urination has completed, the pump is stopped (box 216) and the volume of expelled urine can be calculated. Recorded bladder pressure data (box 217), such as pressure, flow, pump rotations, volume, time and the like, can be transmitted to the digital device 20 (box 218). Optionally, volume can be calculated by the device (box 217).

Figure 8:
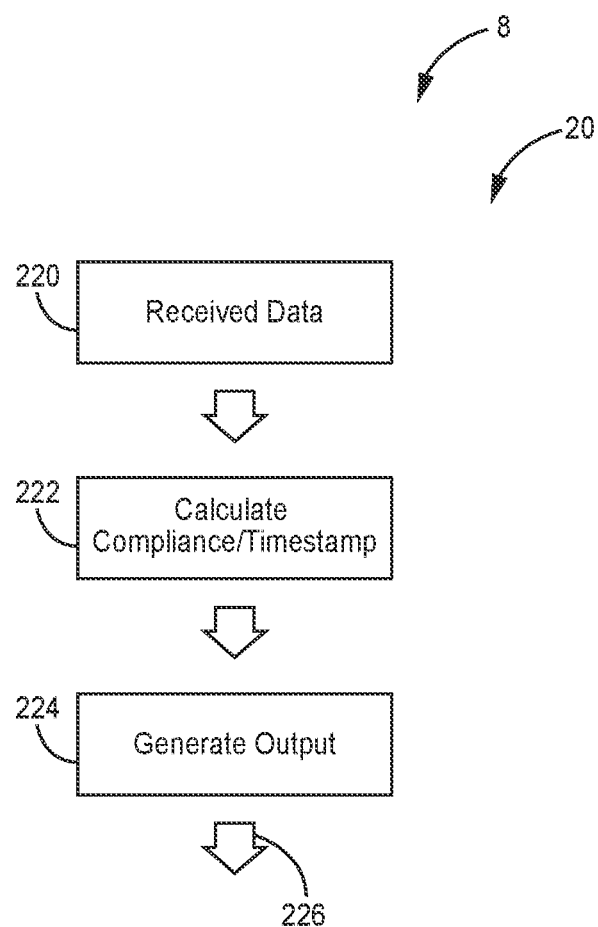
FIG. 8 is a flow chart showing of a mobile device in operation, according to an exemplary implementation.

As shown in FIG. 8, the recorded bladder pressure data is received by the digital device (box 220). Optionally, additional calculations—such as compliance and trending—can be performed (box 222). The digital device is also able to generate output (box 224), which can be viewed by the patient, physician, or other interested party, such as by way of a mobile application or display device (not shown). As has been described previously, in exemplary embodiments, the data can be transmitted by way of a secure connection (shown at 226 in FIG. 8).

By counting the total pump revolutions, the volume of urine within the bladder is determined. As with the pressure only device, the measurements are saved in memory 42A by the processor 40A and can be transmitted to a smartphone app for storage and electronic submission to the treating physician.

Figures 9A, 9B:
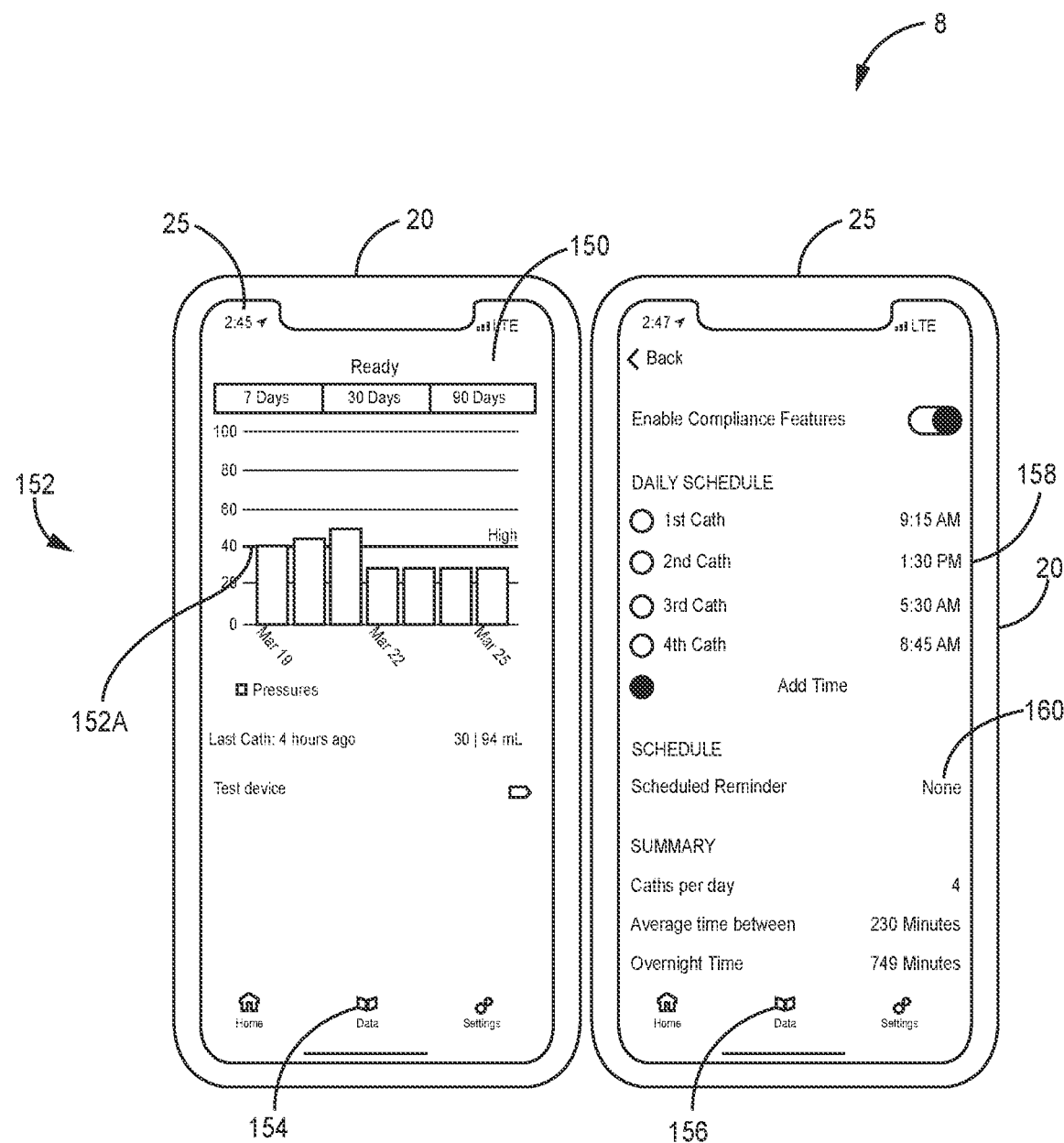
FIG. 9A is a front view of a mobile device operating a software application, according to an exemplary embodiment.
Figure 10A:
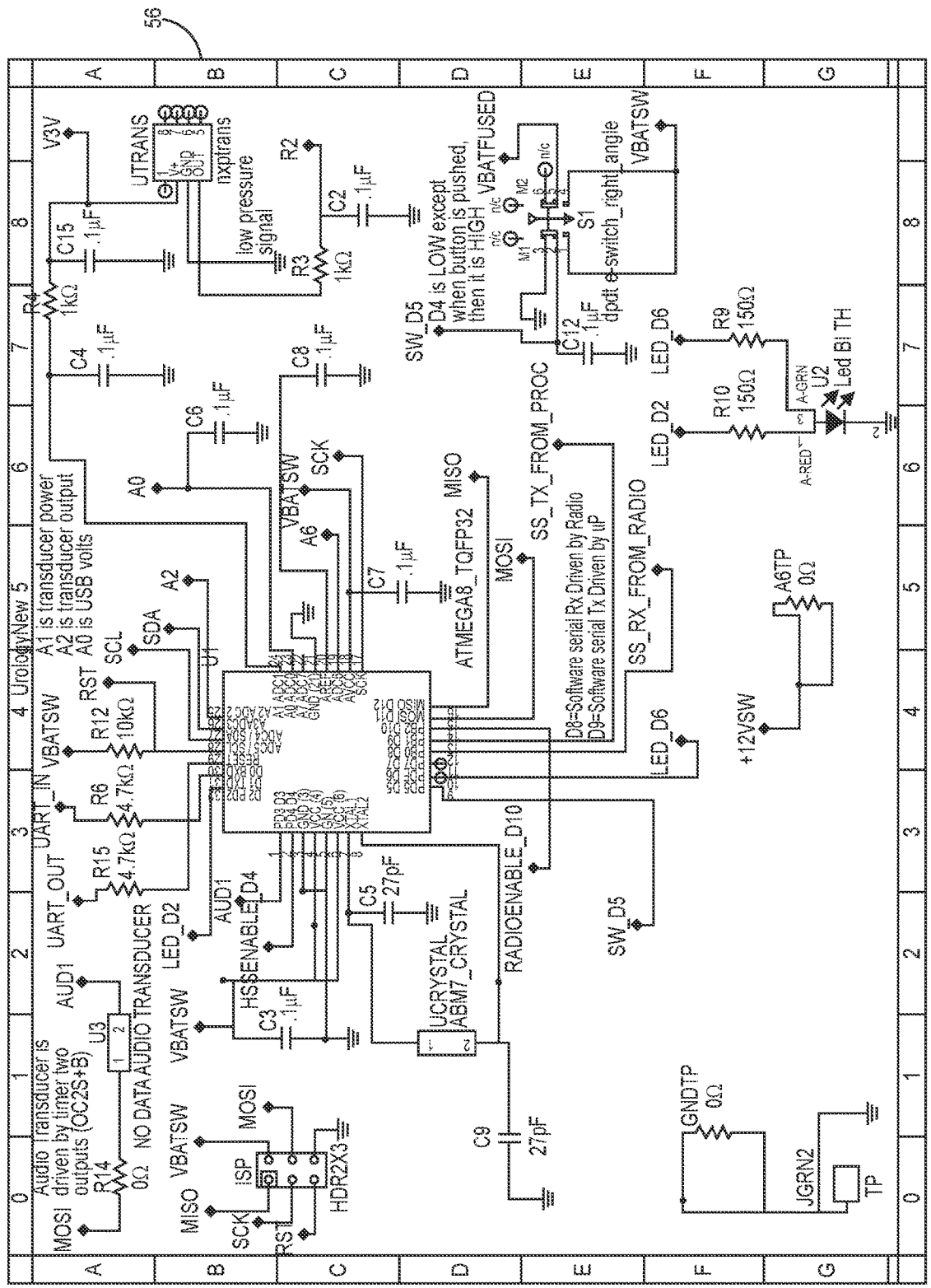
FIG. 10A is a circuit diagram for a PCB according to the bladder pressure sensing device embodiment of FIG. 1B.
Figure 10B:
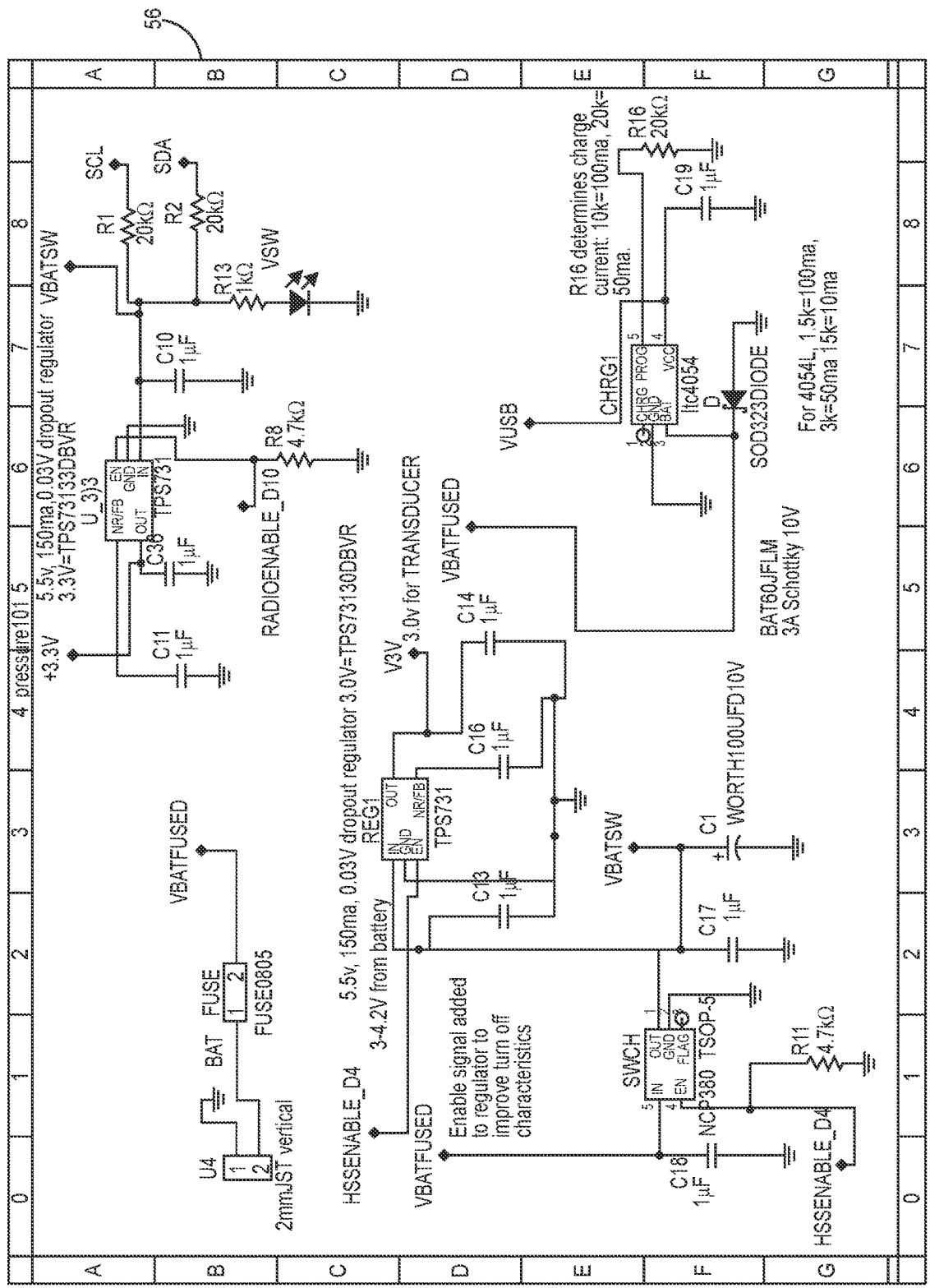
FIG. 10B is a circuit diagram for a PCB according to the bladder pressure sensing device embodiment of FIG. 1B.
Figure 10C:
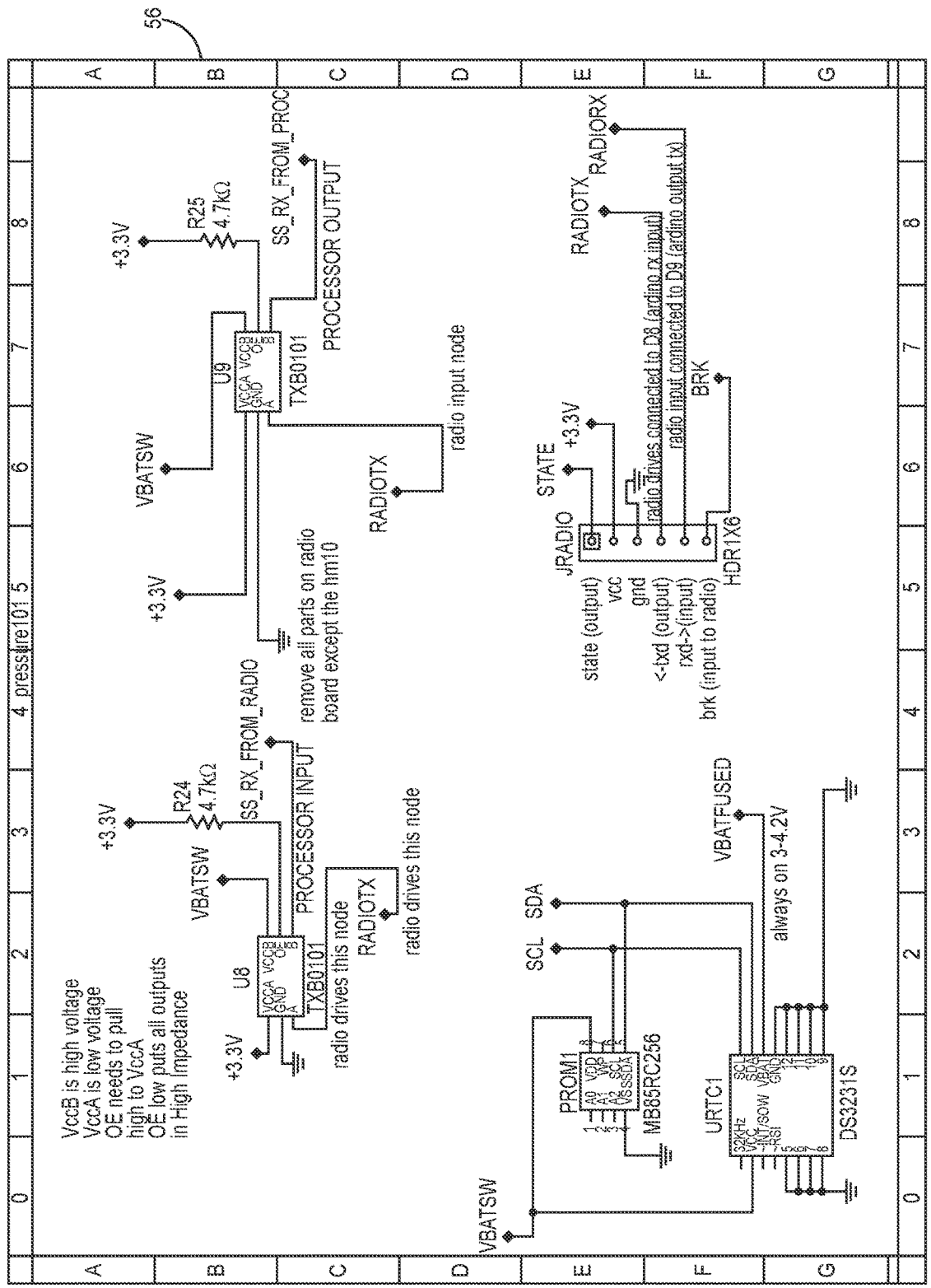
FIG. 10C is a circuit diagram for a PCB according to the bladder pressure sensing device embodiment of FIG. 1B.
Figure 10D:
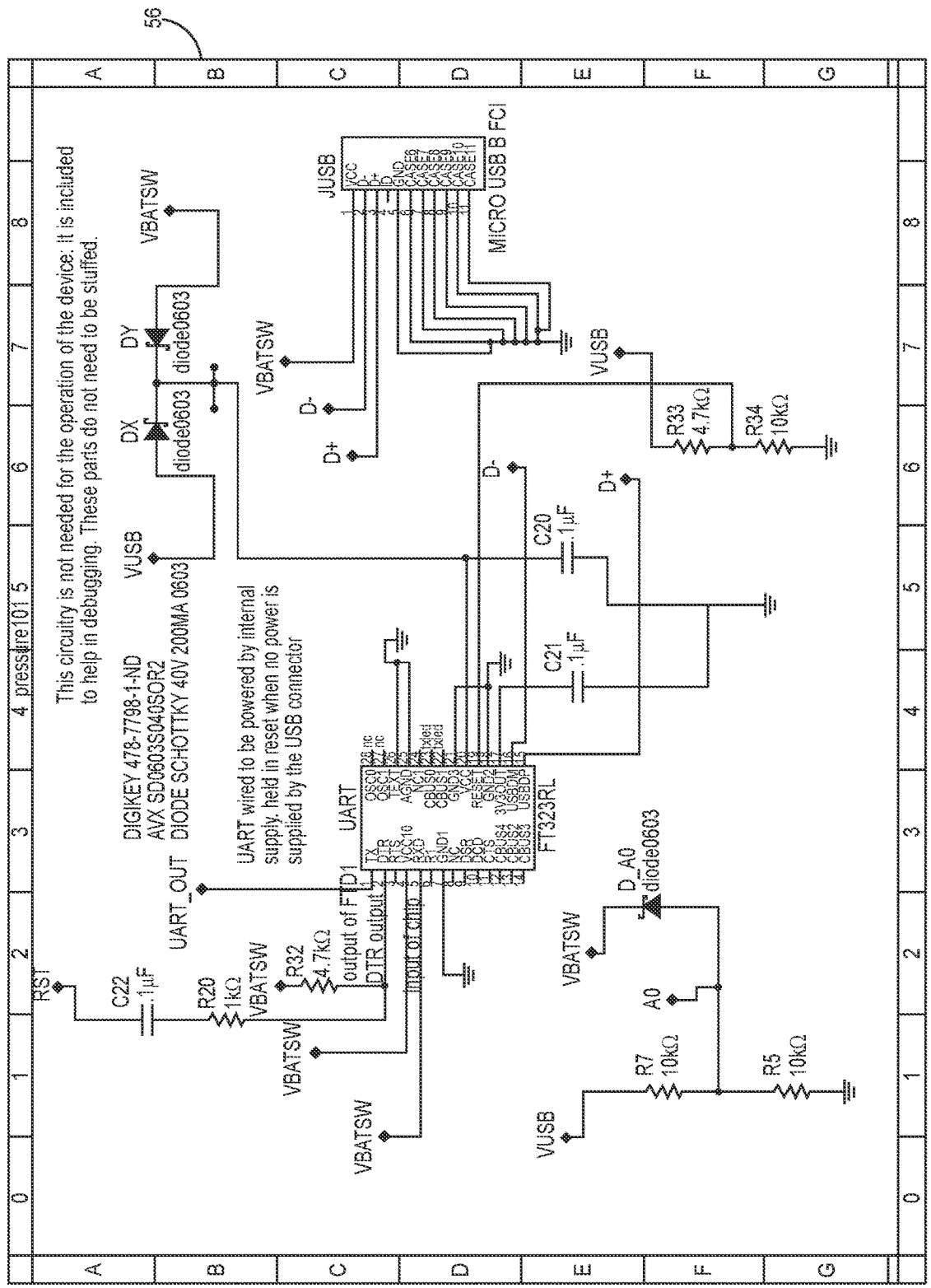
FIG. 10D is a circuit diagram for a PCB according to the bladder pressure sensing device embodiment of FIG. 1B.
Figure 11A:
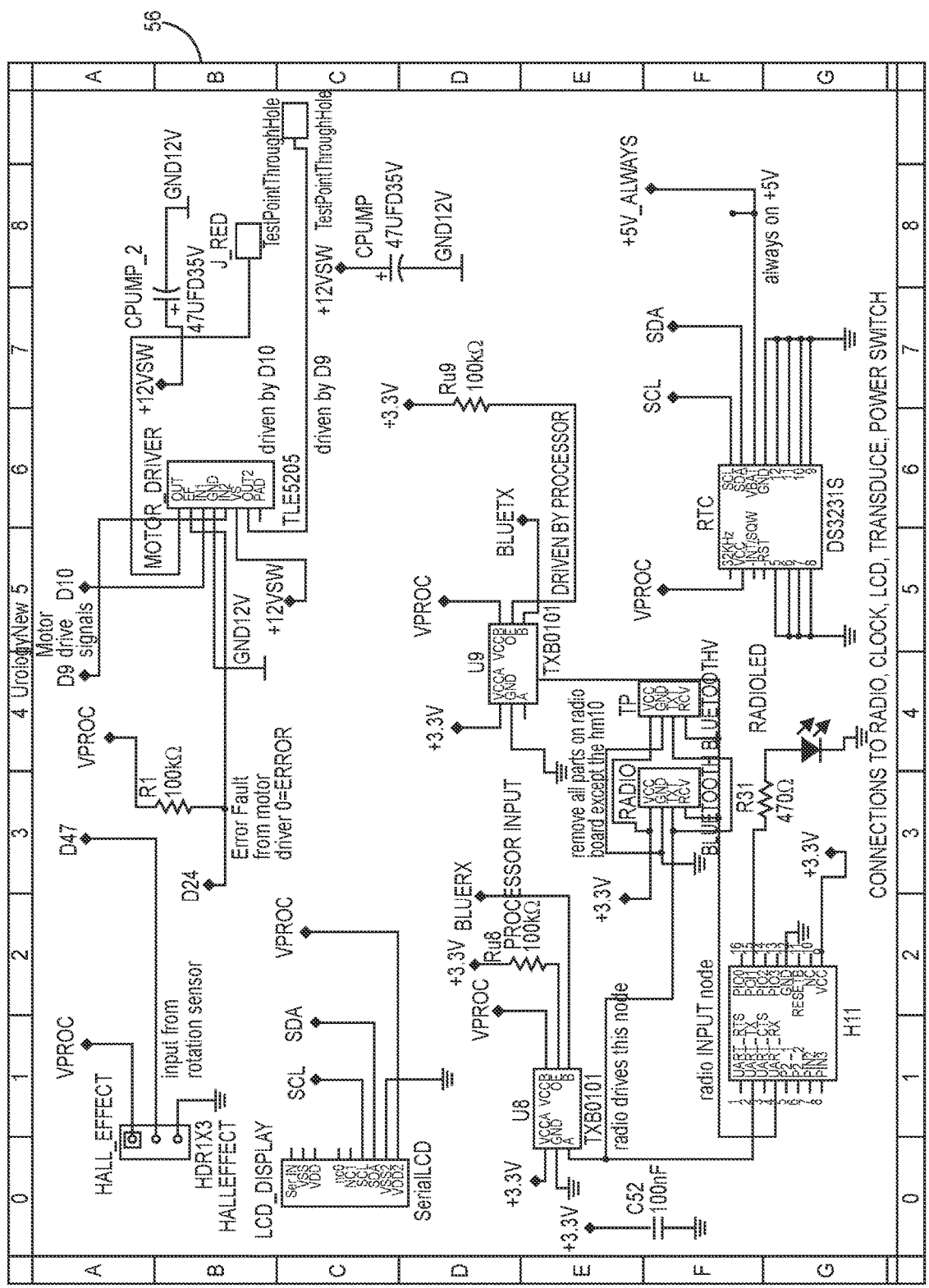
FIG. 11A is a circuit diagram for a PCB according to the bladder pressure sensing device embodiment of FIG. 6.
Figure 11B:
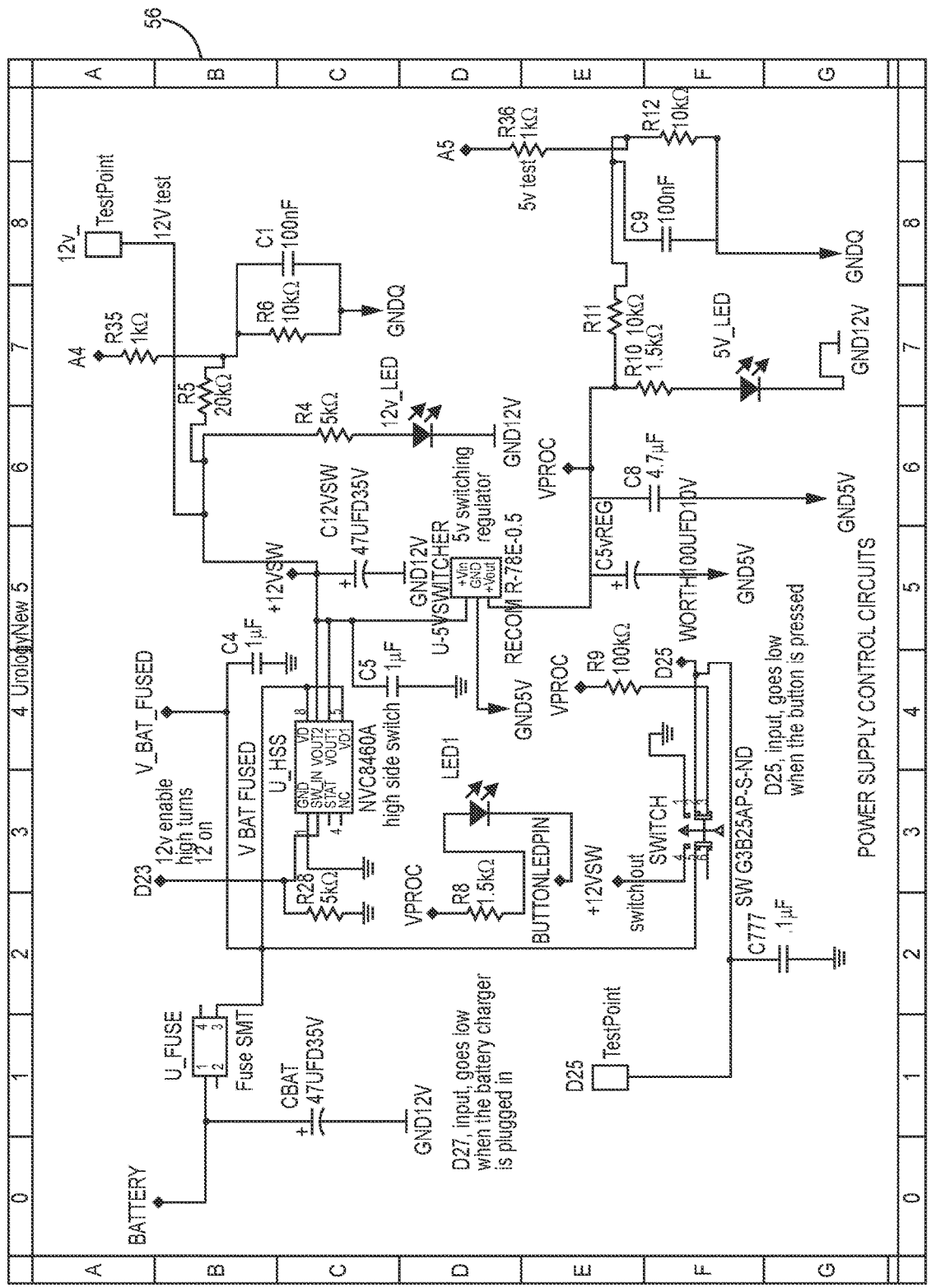
FIG. 11B is a circuit diagram for a PCB according to the bladder pressure sensing device embodiment of FIG. 6.
Figure 11C:
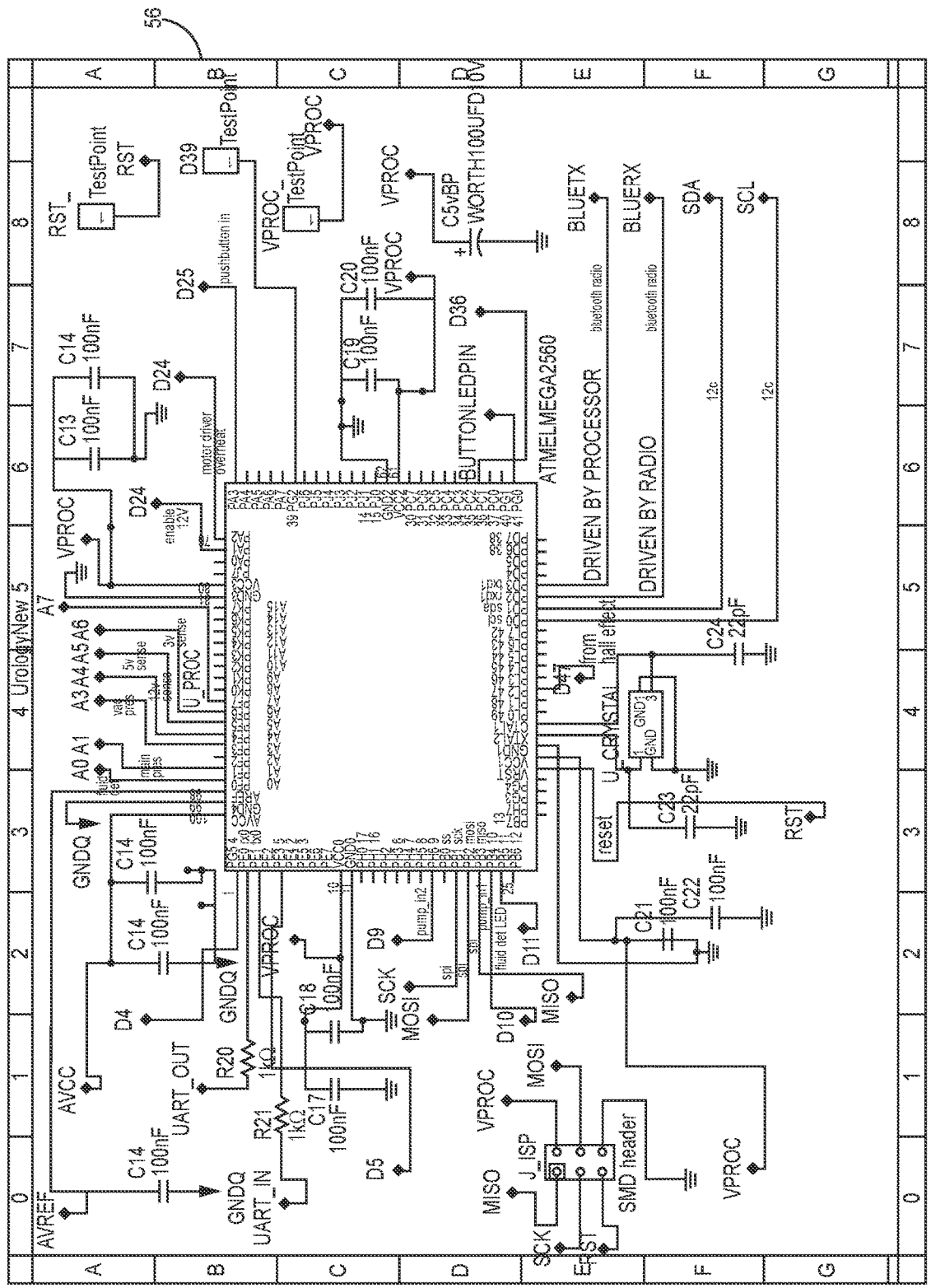
FIG. 11C is a circuit diagram for a PCB according to the bladder pressure sensing device embodiment of FIG. 6.
Figure 11D:
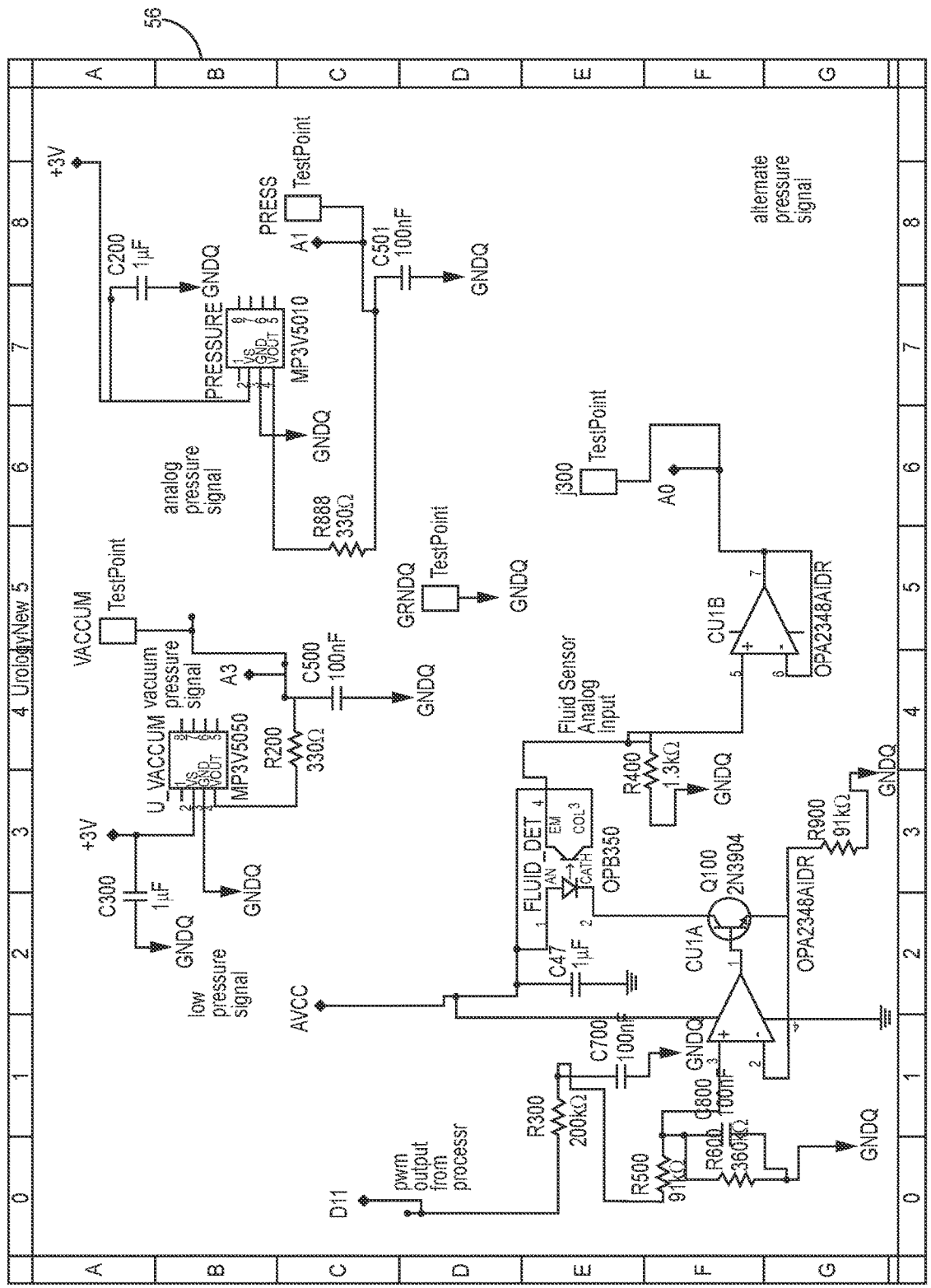
FIG. 11D is a circuit diagram for a PCB according to the bladder pressure sensing device embodiment of FIG. 6.
Figure 11E:
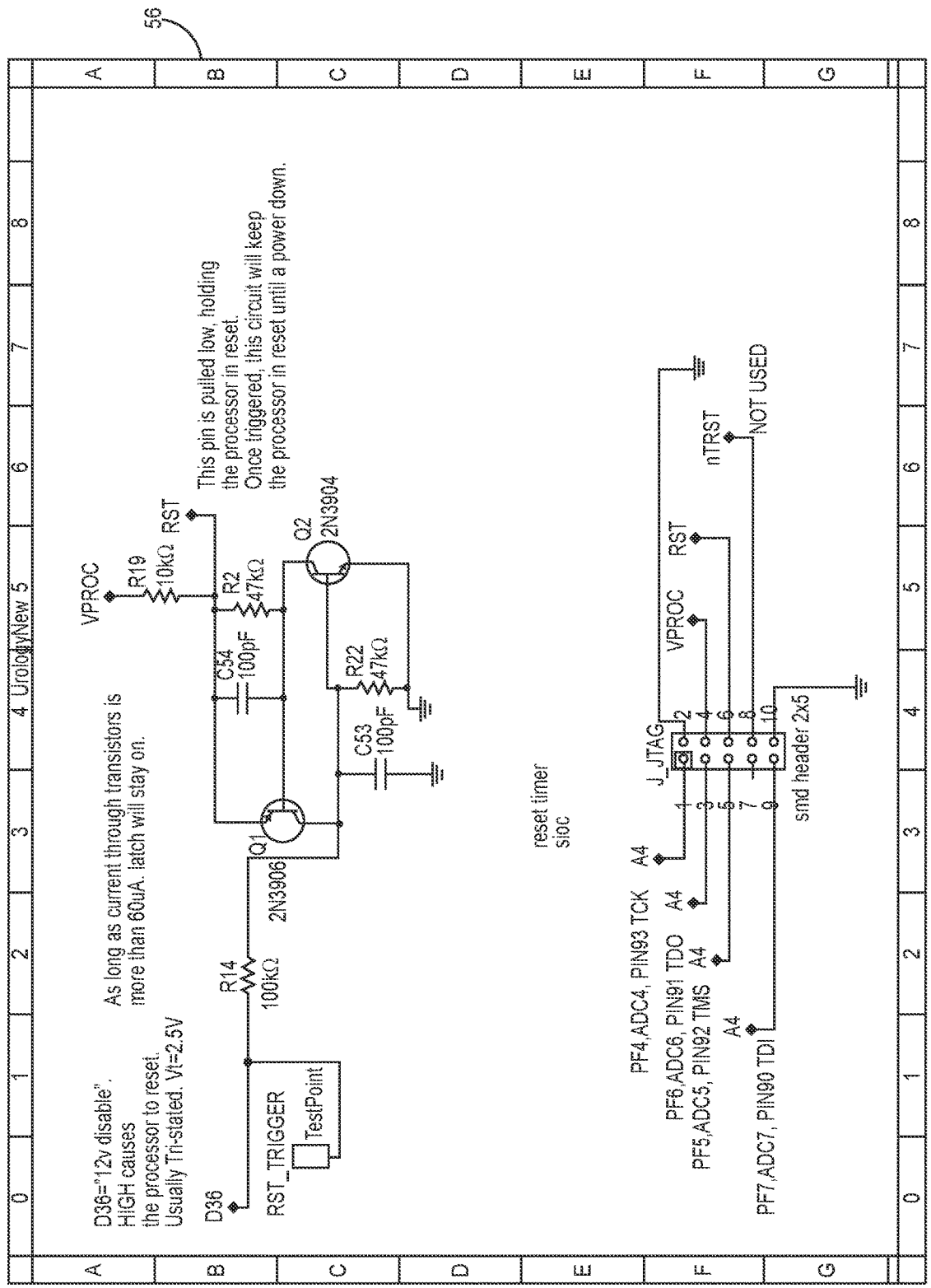
FIG. 11E is a circuit diagram for a PCB according to the bladder pressure sensing device embodiment of FIG. 6.
Figure 11F:
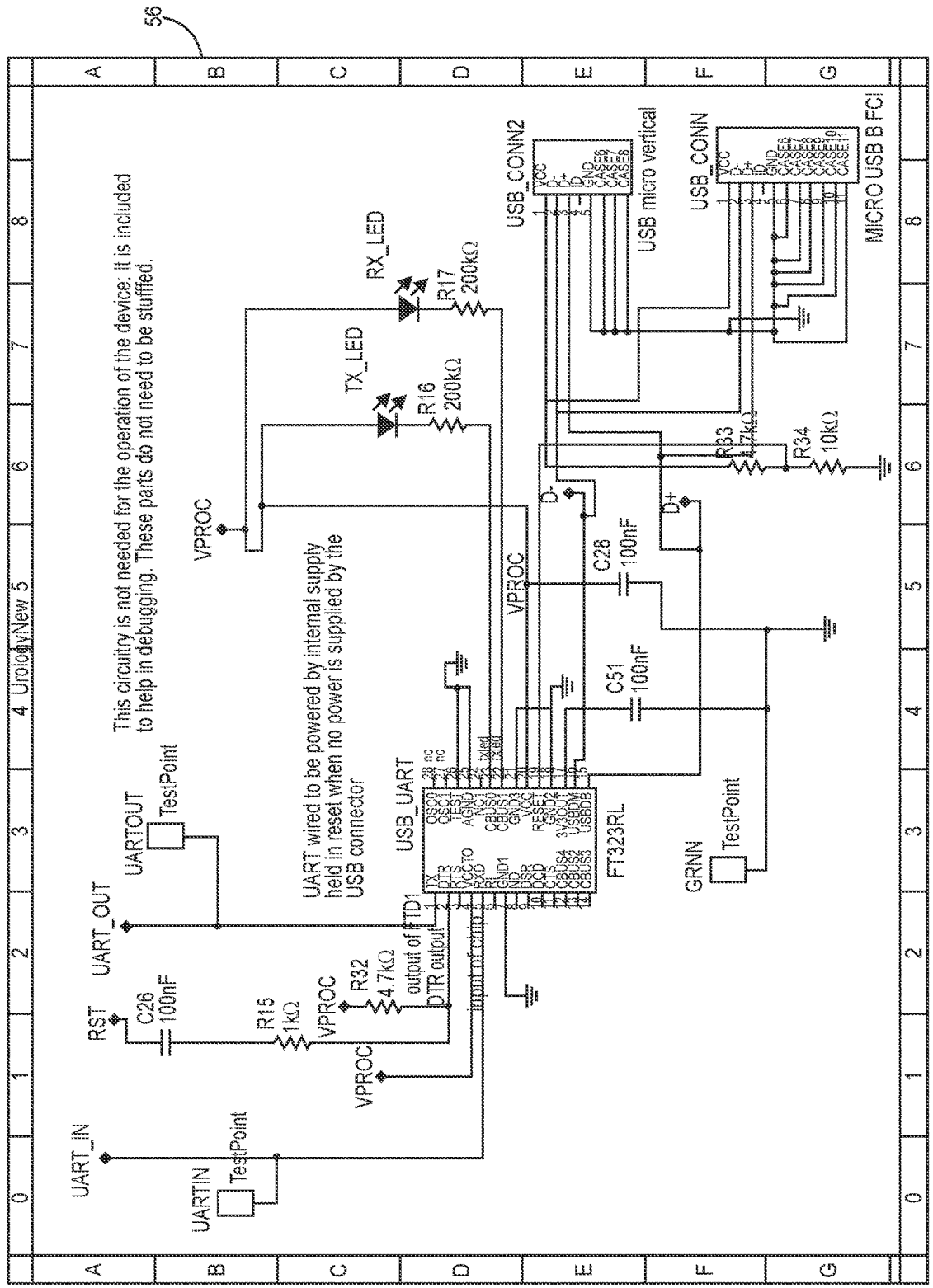
FIG. 11F is a circuit diagram for a PCB according to the bladder pressure sensing device embodiment of FIG. 6.
Figure 11G:
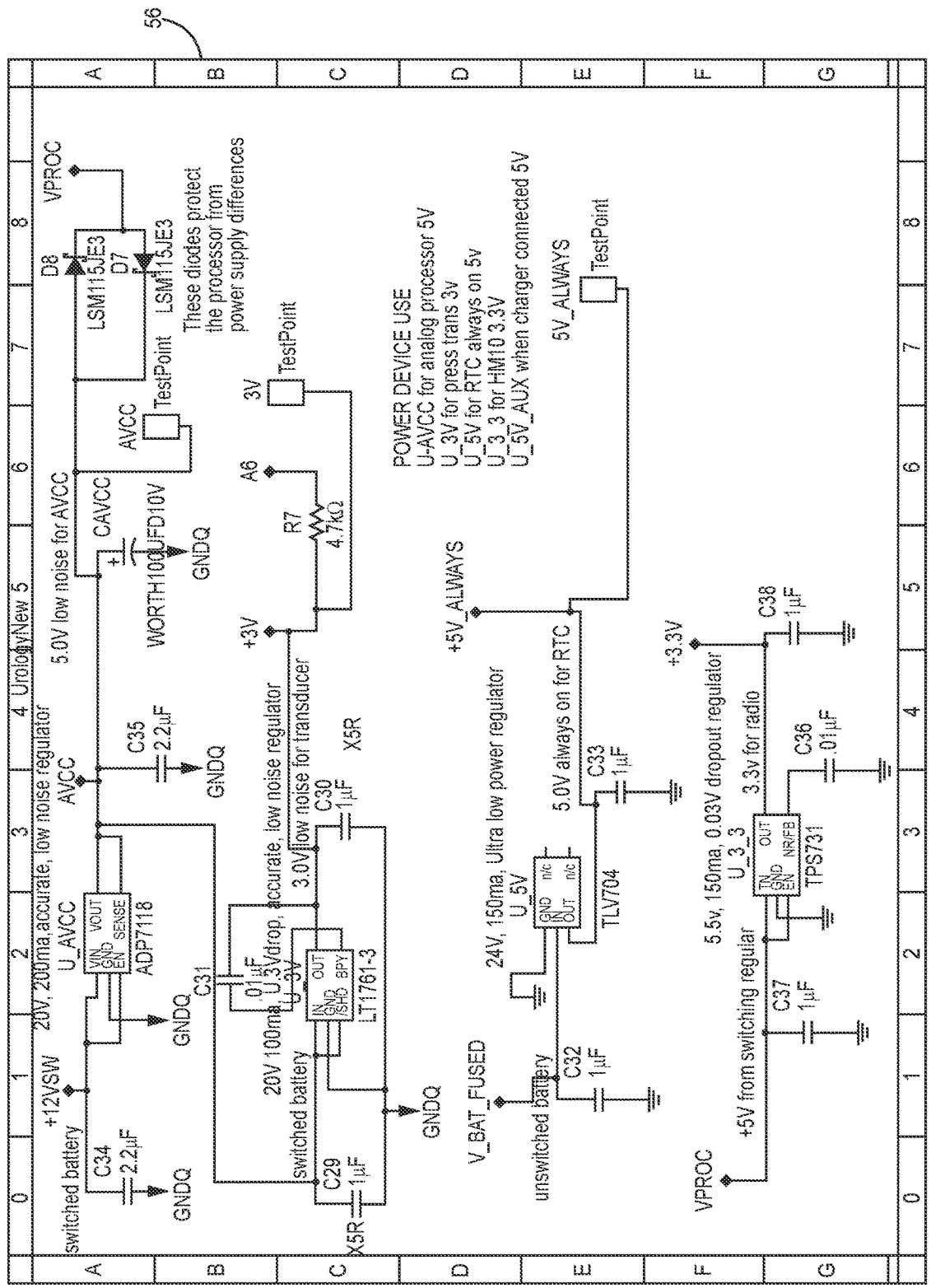
FIG. 11G is a circuit diagram for a PCB according to the bladder pressure sensing device embodiment of FIG. 6.
Figure 11H:
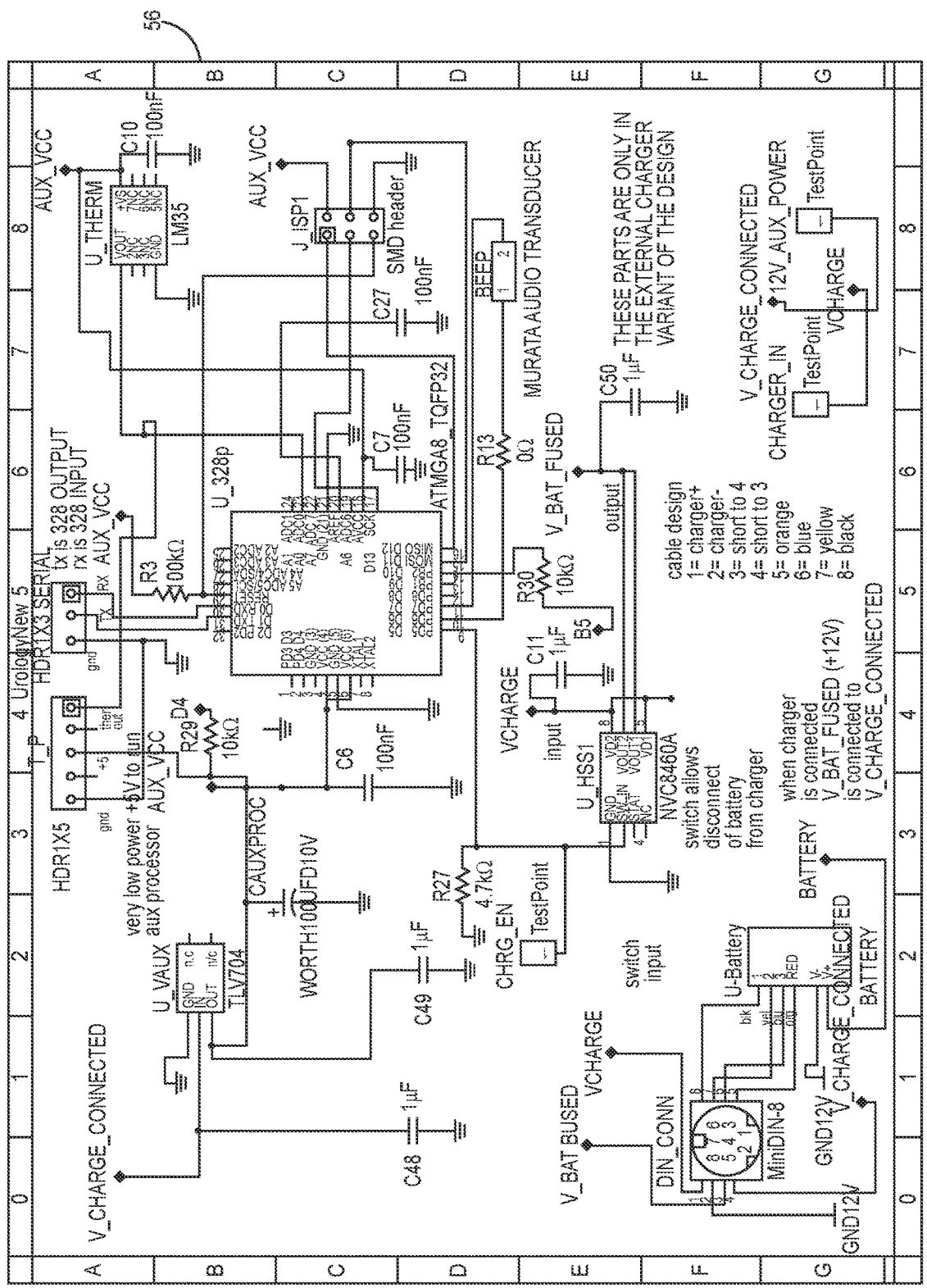
Figure 11I:
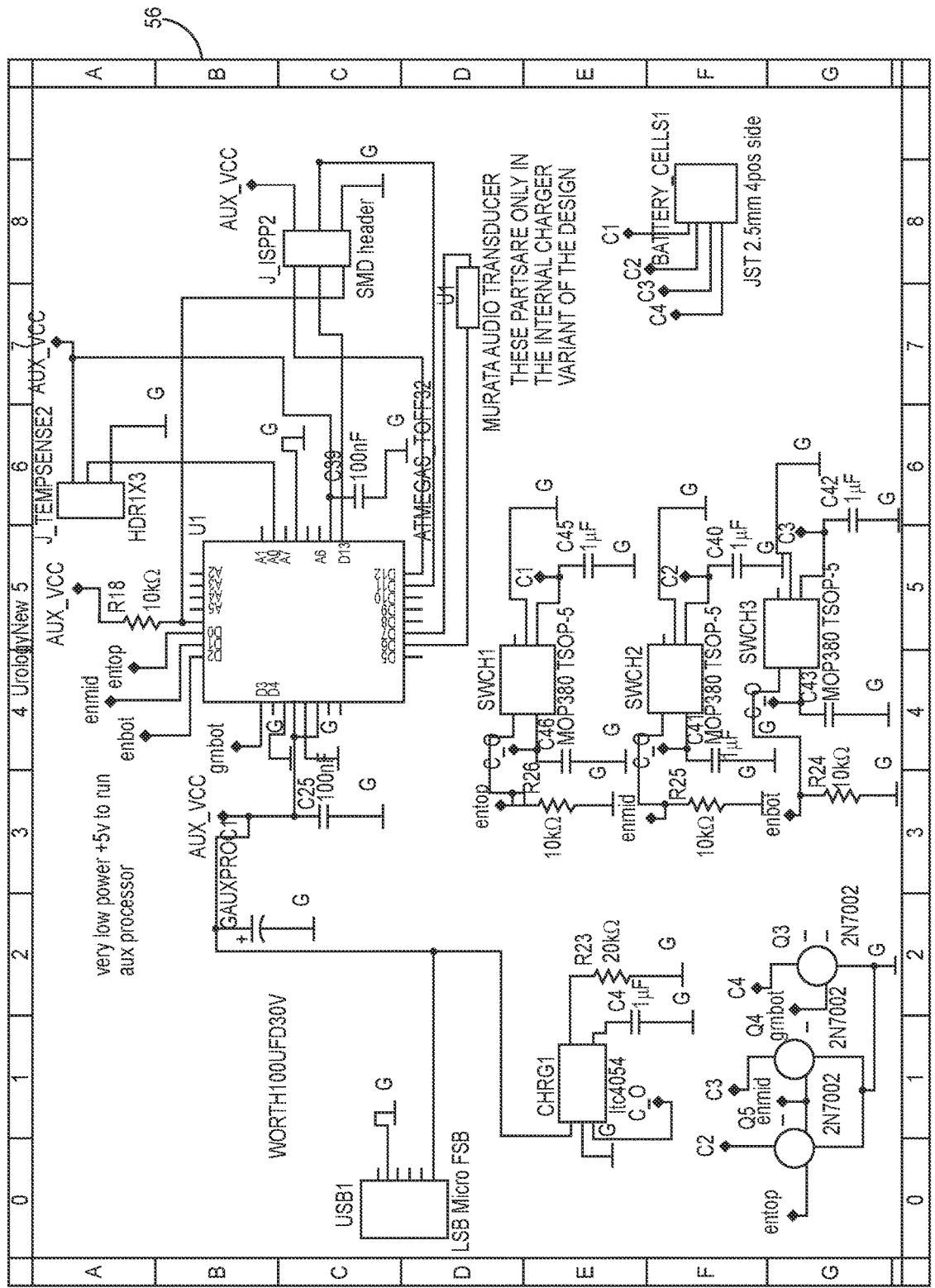

In various implementations of the system 8, a software application 25 is provided that allows the patient or user to assess the health of the bladder and chart bladder pressure. In various implementations, the software application 25 is an app that is installed on the phone or other mobile device 20 of a user, patient or physician, such as is shown in FIGS. 9A-9B. The various processors 40A, 40B and memory 42A, 42B described above are configured to execute the various steps and processes described herein, as would be readily appreciated.

In various implementations, the connection with the device such as via Bluetooth or a cellular or WiFi connection allows the user to download readings and, optionally, transfer the recorded bladder pressure data to a secure hospital server and the treating physician.

As shown in FIG. 9A, the readings can be plotted graphically over time to assess for trends in bladder pressure measures. This information can be provided via a graphical user interface ("GUI") 150.

That is, in various implementations like that of FIG. 9A, the software is configured such that the GUI will display graphical representations of various recorded bladder pressure data 152, optionally including time, date, pressure and in certain implementations volume and pump data. Various implementations of the recorded bladder pressure data 152 can be represented as pressures over a selected period of time, such as over a day/week/month, along with graphical representations of any thresholds 152A, for example denoting pressure thresholds.

Continuing with FIG. 9A, various implementations also record and store patient data 154 such as biographical information and health record information for use in the software 25, as would be readily appreciated.

As shown in FIG. 9B, various implementations of the software 25 are configured to provide notifications 160 or alerts, such as providing the user with a notification if the pressure exceeds a defined threshold, such as above about 40 cmH2O or if the battery needs to be charged.

The user is also able to input various recording data 156 such as whether or not the recording was taken standing, sitting, or laying down.

In various implementations, the user can also program in their routine catheterization schedule 158 into the software 25 and receive notifications 160 from their mobile device 20 when it is time to measure pressure and/or volume, as would be readily appreciated.

Patients may also choose to create a catheterization schedule that will enable the application to remind patients to catheterize, as well as track compliance with catheterization. By displaying the pressure and optional volume readings (for the embodiments of FIGS. 5A-8) with each associated catheterization, patients may be able to connect behaviors to outcomes. In addition to these patient-focused features, the application also supports directly uploading measurements to a database.

Not only do the aforementioned neurogenic bladder patients benefit from this solution, but health care professionals, caregivers, and catheter distributing companies also reap advantages from such a device. The real-time measurement and data storage capabilities of the embodiments enable health care professionals such as physicians to have a means of regularly monitoring the patient's current bladder status without having to complete the invasive and time consuming office, hospital or clinical UDS test. For this same reason, patients benefit in having a system that monitors their condition so that if abnormal readings occur, they can consult their health care provider before irreversible damage to the bladder or renal system results. In addition, the amount of time that patient caregivers require to take patients to hospital clinics for appointments can be substantially decreased. Also, the amount of time that caregivers take to assist patients with catheterizing can be significantly decreased. Further, utilization of UDS testing by way of the present implementations can be reduced, thus reducing routine use of clinical UDS testing and reducing the overall treatment cost.

According to one embodiment, the various system embodiments described herein provide for measurement of pressure in the bladder at the time of catheter insertion. In accordance with other embodiments, the system 8 as described herein provides for earlier detection of harmful changes in bladder pressure, volume and compliance than known technologies, thereby triggering earlier intervention and protection of the kidney and bladder.

In various implementations, the system 8 can be used to assess the patient's compliance with a specified catheterization schedule by examination of the digital record of the timing of catheterization, or alert sent to the health care professional (such as a physician, physician assistant or nurse) when catheterization threshold does not fall within the optimal range set in the mobile device application. Further, adjustments in the frequency or timing of catheterization could also be made based on patterns of urine pressure and/or output.

In additional implementations, the various implementations of the system 8 are configured to permit patient self-monitoring of the patient's bladder health similar to a patient's home monitoring of blood pressure or blood sugars. The system 8 in certain embodiments is configured to notify a patient, caregiver, and/or physician about the status of a patient's bladder health, including whether the health of the bladder is improving, worsening, or staying the same. In this implementation, based on the information provided via the system 8, the physician or patient can intervene and adjust the patient's treatment regime to prevent bladder damage, if needed.

The importance of maintaining safe bladder pressures for patients with a neurogenic bladder has been well established. Home monitoring of bladder pressures in children with has been difficult and intrusive. Although UDS is considered the gold standard for identifying and treating children with lower urinary tract dysfunction, it has been noted to be fraught with artifacts. In addition to these technical challenges in obtaining UDS, a recent study demonstrated significant inter-observer variability during interpretation of video UDS tracings between pediatric urologists. As currently performed and used, UDS is a variable, highly subjective (even amongst experts), snapshot-in-time of bladder function.

Often the limitations of an unreliable test can be improved with repeated measurements, however, the inconvenience and expense of performing multiple frequent UDS in patients is prohibitive. For example, at the author's institution, current hospital charges for urodynamics with fluoroscopy average $6,353 and professional charges average $2,231. Without fluoroscopy, hospital charges average $4,334 and professional charges average $1,126. A recent cost estimate of UDS equipment is almost $140,000 with an additional $190,000 for a fluoroscopy C-arm.

The frequency with which urodynamics are obtained varies. Current recommendations state that UDS should be obtained every 12 months until a child reaches the toddler age, after which testing is prompted by the development of symptoms (change in continence) or signs (hydronephrosis, lower extremity function) concerning for deterioration. However, awaiting signs and symptoms of pathologic changes is suboptimal and reactive rather than proactive. Furthermore, while it has been noted that upper tract changes (hydronephrosis) may be reversible after institution of intermittent catheterization and pharmacologic therapy, bladder compliance changes are less likely to improve, suggesting irreversible changes have occurred.

The various devices systems and methods described herein providing an inexpensive and convenient technology for measuring, tracking, and monitoring bladder pressure in patients using intermittent catheterization. The simplicity of the devices with their single button, along with the automated recording and wireless transfer of data, overcomes some of the inconveniences noted with previously described methods of home bladder pressure measurements. Even for patients without a smart phone, the devices may be used and will store the data for transfer at a later time.

The ability to perform repeated frequent measurements may overcome some of the current limitations of UDS including potentially erroneous information or interpretation obtained by a single point-in-time UDS. These devices may also improve patient compliance with catheterization and medication because of the feedback the patient or caregiver is provided from the device. Physiologic functions demonstrate a pattern of variability throughout the day and it seems likely that urine output and bladder storage dynamics may also demonstrate circadian patterns. With this in mind, the presently-disclosed embodiments may help define these patterns and permit a more tailored catheterization and medication schedule for each individual. Finally, after making a change in bladder management (e.g. catherization frequency, medication dose or schedule), the devices will allow for the effects of the intervention to be better detected, quantified, and recorded.

The novel systems, methods and devices described herein provide accurate bladder pressure and optionally volume measurements. The newly developed device implementations demonstrate accurate bladder pressure measurements and wireless transfer of data to both a smartphone application and secure hospital server. The potential to improve healthcare management and outcomes in patients with a neurogenic bladder through the use of a low cost, easy to use devices, as described above, is extremely high.

The invention claimed is:

1. A bladder health monitoring device comprising:
   (a) a housing defining an enclosure;
   (b) a tube disposed through the enclosure;
   (c) a pressure sensor disposed within the enclosure; and
   (d) an actuation button configured to initiate the measurement of bladder pressure via the pressure sensor.

2. The bladder health monitoring device of claim 1, further comprising a coupling component configured to attach to the end of any catheter routinely used for intermittent catheterization.

3. The bladder health monitoring device of claim 1, further comprising:
   (a) a processor disposed within the enclosure; and
   (b) a radio disposed within the enclosure.

4. The bladder health monitoring device of claim 3, further comprising a PCB disposed within the enclosure and in operable communication with the processor and the radio.

5. The bladder health monitoring device of claim 3, further comprising memory.

6. The bladder health monitoring device of claim 1, further comprising a switch, wherein the actuation button is constructed and arranged to actuate the switch and form a pinch valve with the tube in the enclosure upon actuation.

7. A handheld bladder health monitoring device comprising:
   (a) a housing defining an enclosure;
   (b) a tube disposed through the enclosure;
   (c) a pressure sensor disposed within the enclosure;
   (d) a PCB disposed within the enclosure, the PCB comprising:
      (i) a processor; and
      (ii) a memory component;
   (e) a radio disposed within the enclosure; and
   (f) an actuation button in operable communication with the tube and configured to initiate the measurement of bladder pressure via the pressure sensor as recorded bladder pressure data.

8. The handheld bladder health monitoring device of claim 7, further comprising a switch in operational communication with the pressure sensor and actuation button and constructed and arranged to initiate pressure measurement upon actuation of the actuation button.

9. The handheld bladder health monitoring device of claim 7, wherein the pressure sensor is configured to record pressures in the range of about −10 to about 100.0 $cmH_2O$.

10. The handheld bladder health monitoring device of claim 7, further comprising an indicator.

11. The handheld bladder health monitoring device of claim 7, wherein the actuation button is configured to stop the flow of urine through the lumen upon actuation.

12. The handheld bladder health monitoring device of claim 7, wherein the memory is non-volatile memory.

13. The handheld bladder health monitoring device of claim 7, wherein the radio is a Bluetooth® radio configured to pair to a mobile device for the transmission of recorded bladder pressure data.

14. A bladder health monitoring system comprising:
   (a) the handheld bladder health monitoring device of claim 7; and
   (b) a mobile device software application constructed and arranged to display recorded bladder pressure data.

15. A bladder health monitoring system comprising:
   (a) a tube comprising a lumen;
   (b) a housing comprising:
      (i) a processor comprising memory;
      (ii) at least one pressure sensor in fluidic communication with the lumen;
      (iii) a pump in fluidic communication with the lumen; and
      (iv) an actuation button,
   wherein the processor is configured to record bladder pressure data from the at least one pressure sensor when urine has entered the lumen, and
   wherein the processor is configured to, in order,
      (i) begin pumping at a first speed,
      (ii) detect the presence of fluid in the tube lumen,
      (iii) stop pumping,
      (iv) measure and record bladder pressure data, and
      (v) restart pumping at a second speed.

16. The bladder health monitoring system of claim 15, further comprising a fluid detector.

17. The bladder health monitoring system of claim 15, further comprising a second pressure sensor configured to record vacuum pressure during pumping.

18. The bladder health monitoring system of claim 15, further comprising a Bluetooth® radio configured to pair to a mobile device for the transmission of recorded bladder pressure data.

19. The bladder health monitoring system of claim 15, further comprising at least one indicator.

* * * * *